US008894567B2

(12) United States Patent
Honda et al.

(10) Patent No.: US 8,894,567 B2
(45) Date of Patent: Nov. 25, 2014

(54) MEDICAL TUBE

(75) Inventors: Kazuki Honda, Hachioji (JP); Yasuhito Kura, Hachioji (JP); Wataru Matsuura, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 318 days.

(21) Appl. No.: 12/813,814

(22) Filed: Jun. 11, 2010

(65) Prior Publication Data

US 2011/0004060 A1      Jan. 6, 2011

Related U.S. Application Data

(63) Continuation of application No. PCT/JP2009/068983, filed on Nov. 6, 2009.

(30) Foreign Application Priority Data

Feb. 9, 2009   (JP) ................................. 2009-027545

(51) Int. Cl.
| A61B 1/00 | (2006.01) |
| A61B 1/04 | (2006.01) |
| A61B 1/273 | (2006.01) |
| A61M 25/06 | (2006.01) |
| A61M 25/00 | (2006.01) |

(52) U.S. Cl.
CPC ........... *A61B 1/2736* (2013.01); *A61B 1/00078* (2013.01); *A61M 2025/0681* (2013.01); *A61B 1/00135* (2013.01); *A61M 25/0074* (2013.01); *A61M 25/007* (2013.01)
USPC ............................ 600/129; 600/114; 600/127

(58) Field of Classification Search
CPC ..................... A61B 1/00078; A61B 1/00135
USPC ......... 600/106, 114, 121, 123, 125, 130, 139, 600/143, 144, 153, 127, 129; 604/536
See application file for complete search history.

(56) References Cited

U.S. PATENT DOCUMENTS

| 4,329,980 A | 5/1982 | Terada |
| 5,025,778 A * | 6/1991 | Silverstein et al. ........... 600/104 |

(Continued)

FOREIGN PATENT DOCUMENTS

| EP | 1 787 575 A1 | 5/2007 |
| JP | 55-118731 | 9/1980 |

(Continued)

OTHER PUBLICATIONS

Extended Supplementary European Search Report dated Jan. 17, 2013 in European Patent Application No. 09839697.1.

*Primary Examiner* — Alireza Nia
(74) *Attorney, Agent, or Firm* — Scully, Scott, Murphy & Presser, PC

(57) ABSTRACT

A medical tube includes: a tube main body through which a conduit, through which an insertion portion of a cholangioscope is insertable, is pierced from a distal end to a rear end; a side hole that is formed between the distal end and the rear end of the tube main body and causes an outer circumferential side of the insertion portion and the conduit to communicate with each other; and a hardness changing portion that can change the hardness of at least a part of the tube main body including the side hole according to operation by an operator.

8 Claims, 25 Drawing Sheets

(56) References Cited

U.S. PATENT DOCUMENTS

| | | | |
|---|---|---|---|
| 5,392,766 A * | 2/1995 | Masterson et al. | 600/157 |
| 5,702,348 A * | 12/1997 | Harhen | 600/124 |
| 6,142,931 A * | 11/2000 | Kaji | 600/114 |
| 7,654,951 B2 * | 2/2010 | Ishikawa | 600/114 |
| 7,857,749 B2 * | 12/2010 | Ouchi | 600/104 |
| 2005/0240147 A1 | 10/2005 | Makower et al. | |
| 2006/0207608 A1 | 9/2006 | Hirotsuka et al. | |
| 2007/0149852 A1 | 6/2007 | Noguchi et al. | |
| 2008/0033244 A1 * | 2/2008 | Matsui et al. | 600/114 |
| 2009/0030284 A1 * | 1/2009 | Cole et al. | 600/206 |

FOREIGN PATENT DOCUMENTS

| | | |
|---|---|---|
| JP | 55-155629 | 12/1980 |
| JP | 60-185532 | 9/1985 |
| JP | 01-28581 | 6/1989 |
| JP | 05-056910 | 3/1993 |
| JP | 07-184836 | 7/1995 |
| JP | 09-285441 | 11/1997 |
| JP | 10-118011 | 5/1998 |
| JP | 11-076182 | 3/1999 |
| JP | 11-104066 | 4/1999 |
| JP | 2000-342528 | 12/2000 |
| JP | 2003-038421 | 2/2003 |
| JP | 2004-041700 A | 2/2004 |
| JP | 2007-029291 | 2/2007 |
| WO | WO 03/041782 A1 | 5/2003 |
| WO | WO 2006/028019 A1 | 3/2006 |

* cited by examiner

MEDICAL TUBE

CROSS-REFERENCE TO RELATED APPLICATION

This application is a continuation application of PCT/JP2009/068983 filed on Nov. 6, 2009 and claims the benefit of Japanese Application No. 2009-027545 filed in Japan on Feb. 9, 2009, the entire contents of each of which are incorporated herein by their reference.

BACKGROUND OF THE INVENTION

1. Field of the Invention

The present invention relates to a medical tube for guiding a medical instrument inserted into a body cavity.

2. Description of the Related Art

In general, bloodless treatment for choledocholithiasis is performed by endoscopic transduodenal sphincterotomy is performed. However, there are not few cases of complication of choledocholithiasis and hepatolithiasis. In some case, treatment for hepatolithiasis is necessary even after removal of choledocholith by the endoscopic transduodenal sphincterotomy. Therefore, there is a demand for diagnosis of hepatholithiasis and bloodless treatment by peroral cholangioscopy.

However, when an endoscope representing a medial instrument inserted from the stomach side is set as a reference, the exit opening of a biliary tract is directed in a return direction with respect to a duodenum. Therefore, when it is attempted to insert the endoscope into the biliary tract, endoscope operation is difficult because it is necessary to insert the endoscope while bending a distal end of the endoscope to the back.

As a measure against this problem, for example, as disclosed in Japanese Examined Patent Application Publication No. 01-28581, there is known a technique for leading an endoscope into the biliary tract in a transpapillary manner using a flexible tubular member (an over tube).

A tubular member 101 disclosed in the document is shown in FIG. 41. As shown in the figure, when the peroral cholangioscopy is performed by using an endoscope, first, the tubular member 101 is inserted into an insertion portion of a not-shown endoscope for duodenum of a side-view type in advance. A distal end of the insertion portion of the endoscope projected from a distal end of this tubular member 101 is inserted to a papilla A (a duodenal papilla A) of a duodenum 104 in an observation direction. When the duodenal papilla A is confirmed by the endoscope for duodenum, the tubular member 101 is moved forward to bring a side hole 101a opened on the outer side of this tubular member 101 into a field of view of the endoscope for duodenum.

Thereafter, the endoscope for duodenum is pulled out and, instead, a cholangioscope 102 is inserted into this tubular member 101 and a distal end of an insertion portion 103 of this cholangioscope 102 is led to the side hole 101a. When the distal end of the insertion portion 103 is faced to the side hole 101a, the insertion portion 103 is bent and the distal end of the insertion portion 103 is inserted through the side hole 101a, led to the duodenal papilla A through this side hole 101a, and inserted into a choledoch B from this duodenal papilla A. An advancing direction of the insertion portion 103 of the cholangioscope 102 is led into the choledoch B with a distal end side edge P1 of this side hole 101a as a fulcrum.

SUMMARY OF THE INVENTION

A medical tube according to the present invention includes: a flexible and bendable tubular member through which a conduit, through which a medical instrument is insertable, is pierced from a distal end to a rear end; and a side hole that is formed between the distal end and the rear end of the tubular member and causes an outer circumferential side of the tubular member and the conduit to communicate with each other. The tubular member includes a hardness changing portion that can change rigidity with respect to a direction having a center in a vicinity of the side hole and orthogonal to an axis direction of the tubular member.

BRIEF DESCRIPTION OF THE DRAWINGS

FIGS. 1 to 10 show a first embodiment of the present invention, wherein FIG. 1 is a schematic diagram of a medical tube and an endoscope;

FIG. 4 is a IV-IV sectional view of FIG. 3B;

FIG. 5 is an explanatory diagram of a state in which the medical tube and an insertion portion of the endoscope is inserted into a duodenum;

FIG. 6 is an explanatory diagram of a state in which the side hole of the medical tube is opposed to a duodenal papilla;

FIG. 7 is an explanatory diagram of a state in which a distal end of the endoscope insertion portion is retracted from a distal end portion of the medical tube;

FIG. 8 is an explanatory diagram of a state in which the distal end of the endoscope insertion portion is projected from the side hole of the medical tube;

FIG. 9 is an explanatory diagram of a state in which the distal end of the endoscope insertion portion is led to a choledoch in a transpapillary manner;

FIG. 10 is an explanatory diagram showing a region of the tube main body where rigidity is at least necessary;

FIGS. 11A to 16B show a second embodiment of the present invention, wherein FIG. 11 is a perspective view of a distal end portion of a medical tube;

FIG. 13 is a sectional side view of a fixing section;

FIG. 14 is a sectional side view in another state of FIG. 13;

FIG. 15 is a main part perspective view of a state in which a distal end portion of a tube main body is deformed;

FIG. 16B is a main part right side view of FIG. 16A;

FIGS. 18A to 22B show a fourth embodiment of the present invention, wherein FIG. 18A is a sectional side view of a distal end portion of a medical tube;

FIG. 19 is a sectional side view of a rear end portion of the medical tube;

FIG. 21 is a sectional side view in another state of FIG. 19;

FIG. 22B is a XXII-XXII sectional view of FIG. 22A;

FIGS. 23A to 24B show a distal end portion of a medical tube according to a fifth embodiment of the present invention, wherein FIG. 23A is a sectional side view of the distal end portion of the medical tube;

FIG. 24B is a perspective view after the deformation of the core member;

FIGS. 25A to 26 show a sixth embodiment of the present invention, wherein FIG. 25A is a perspective view before deformation of a hardness changing portion;

FIG. 26 is a sectional front view of the hardness changing portion;

FIGS. 27 to 33B show a seventh embodiment of the present invention, wherein FIG. 27 is a perspective view of a distal end portion of a medical tube;

FIG. 28 is a side view of the distal end portion of the medical tube;

FIG. 29 is a sectional side view of the distal end portion of the medical tube;

FIG. 30 is a perspective view of a hardness changing portion before deformation;

FIG. 31 is a perspective view of the hardness changing portion after the deformation;

FIG. 33B is the B-B section of FIG. 28 and is a sectional view of the hardness changing portion after the deformation;

FIGS. 34A to 36B show an eighth embodiment of the present invention, wherein FIG. 34A is a sectional side view of a distal end portion of a medical tube;

FIG. 35 is a perspective view of a hardness changing portion;

FIG. 36B is a XXXVI-XXXVI sectional view of FIG. 36A;

FIGS. 37 to 40B show a ninth embodiment of the present invention, wherein FIG. 37 is a perspective view of a distal end portion of a medical tube;

FIG. 40B is a perspective view of a state in which the support plate is projected.

DETAILED DESCRIPTION OF THE PREFERRED EMBODIMENTS

Figure 1:
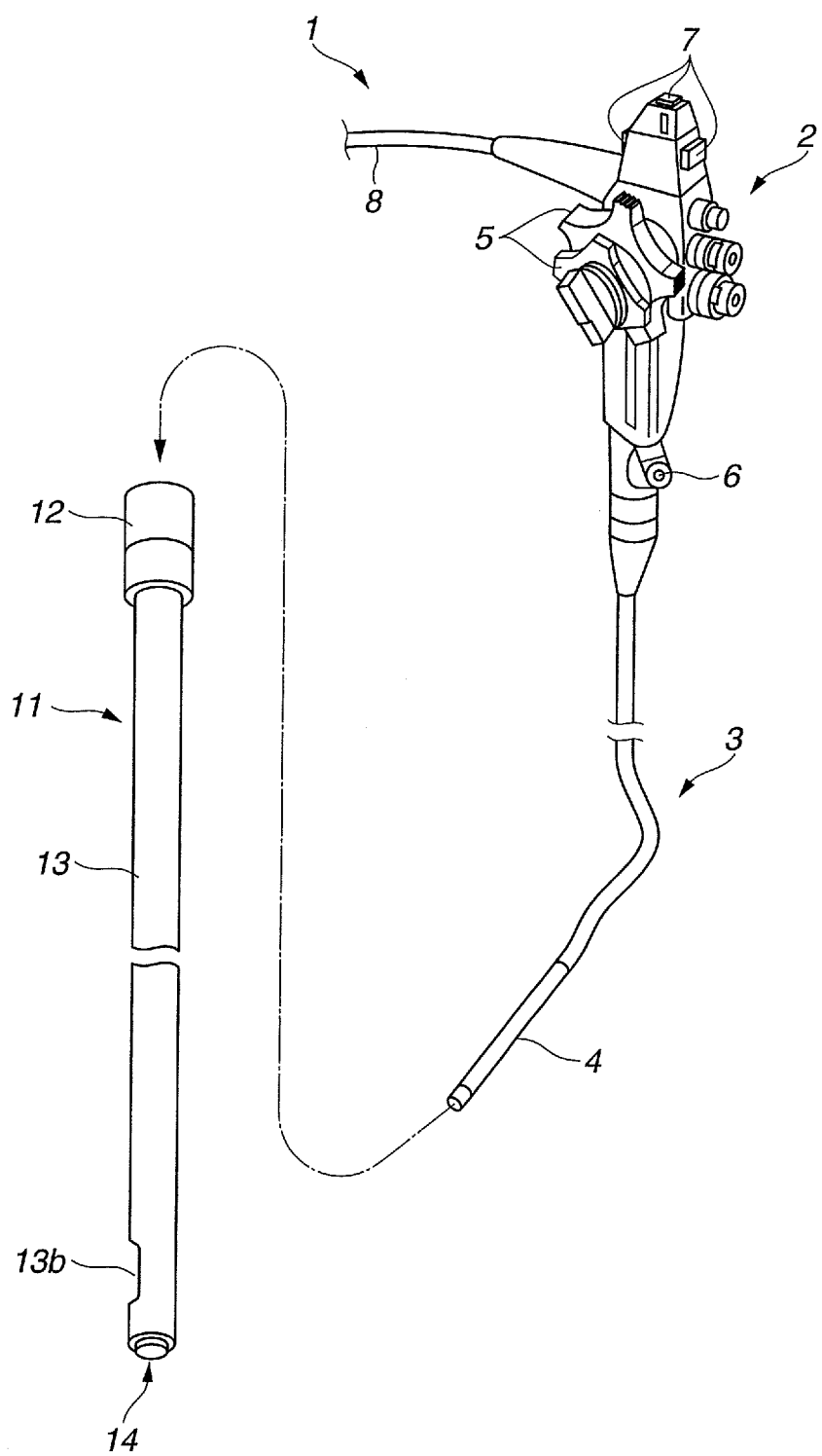

An embodiment of the present invention is explained below on the basis of the drawings.

First Embodiment

A first embodiment of the present invention is shown in FIGS. 1 to 10.

Reference numeral 1 in the figures denotes an endoscope representing a medical instrument. In the present embodiment, a cholangioscope is shown. Therefore, in the following explanation, this endoscope 1 is explained while being referred to as cholangioscope 1.

This cholangioscope 1 has an operation section 2 on a user's hand side. A flexible insertion portion 3 is extended out from this operation section 2. In the operation section 2, a bending operation knob 5 for operating to bend a bending portion 4 provided at a distal end portion of the insertion portion 3 and an insertion port 6 of a treatment instrument insertion channel, through which a treatment instrument and the like are inserted, are provided. At an end of this operation section 2, a universal cord 8 that is connected to a light source device (not shown) and can transmit illumination light and various signals is extended out. The illumination light from the light source device is led in a distal end direction of the insertion portion 3 via this universal cord 8. An illumination optical system, an observation optical system such as an image pickup element, a distal end opening of the treatment instrument insertion channel, and the like (all of which are not shown) are provided at the distal end of the insertion portion 3. An image pickup signal obtained by the image pickup element is transmitted to a processor (not shown) via the universal cord 8 or the like, whereby an observation image is generated. Further, a remote switch 7 for performing remote operation of the processor and a recording device and the like connected to the processor is provided in the operation section 2.

A medical tube (an over tube) 11 is sheathed over this insertion portion 3. In this medical tube 11, a fixing section 12 is provided on a rear end side and a tube main body 13 as a tubular member is extended out from a distal end of this fixing section 12. This tube main body 13 is formed of a flexible material such as soft vinyl chloride or silicon rubber. A conduit 13a, through which the insertion portion 3 provided in the cholangioscope 1 can be inserted, is formed to pierce through from a distal end 3a to a rear end in the inside of the tube main body 13. This tube main body 13 is formed in a cylindrical shape. An outer circumferential side and an inner circumferential side forming the conduit 13a are formed in a coaxial shape. Therefore, the thickness of this tube main body 13 is substantially fixed over an entire circumference.

A side hole 13b that causes the conduit 13a and the outer circumferential side to communicate with each other is opened between the distal end and the rear end of this tube main body 13. This side hole 13b exposes the distal end 3a of the insertion portion 3 inserted through the conduit 13a to the outside. Therefore, specifically, this side hole 13b is formed on a distal end side of the tube main body 13, larger than the outer diameter of the insertion portion 3, and in a long hole shape extending along a major axis (an axis of the conduit 13a).

Further, a hardness changing portion 14 is provided at the distal end of this tube main body 13. As shown in FIGS. 2A, 2B, 3A, and 3B, this hardness changing portion 14 has a so-called spring mouth structure in which both ends of a pair of leaf springs 14a and 14b are supported via hinges 14c. Both the hinges 14c are disposed in an axis direction in which an outer circumferential side on which the side hole 13b is opened and an outer circumferential side opposed to this outer circumferential side are connected. As shown in FIG. 3A, the leaf springs 14a and 14b not applied with external force always maintain a closed state with the resilient force of the leaf springs 14a and 14b. A distal end portion 13c of the tube main body 13 is elastically deformed in a straight line shape to both the hinges 14c side.

Figure 2A:
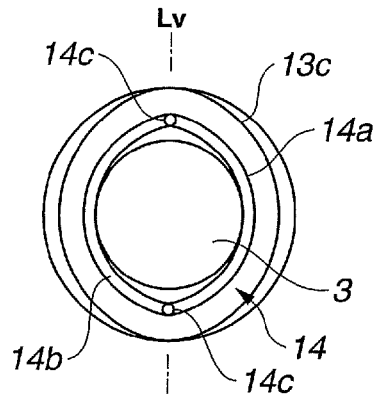
FIG. 2A is a front view of the medical tube and the endoscope.
Figure 2B:
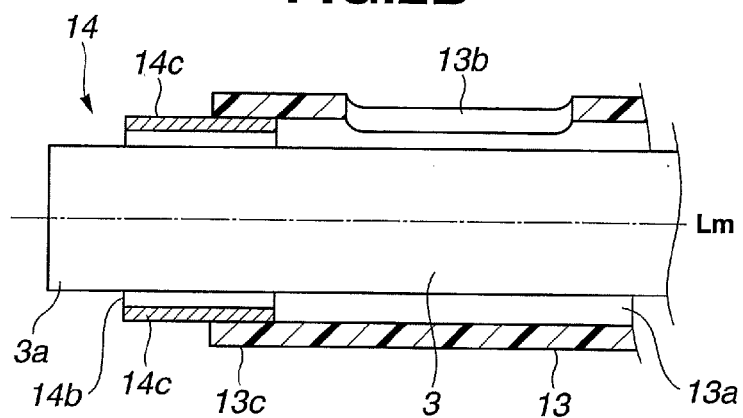
FIG. 2B is a main part right side sectional view of FIG. 2A.
Figure 3A:
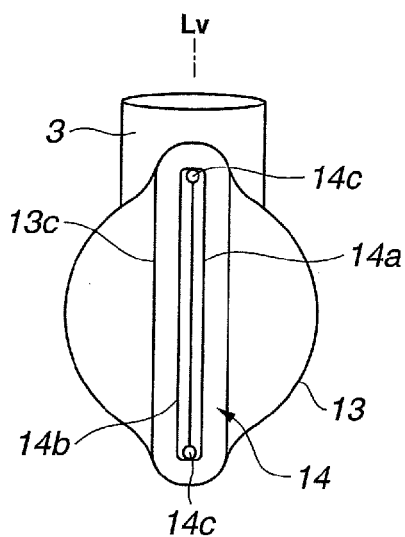
FIG. 3A is a front view of a state in which a distal end of the endoscope is projected from a side hole of a tube main body.

As shown in FIGS. 2A and 2B, in this hardness changing portion 14, the distal end 3a of the insertion portion 3 of the cholangioscope 1 inserted through the conduit 13a is inserted and held. In a state in which the distal end 3a of the insertion portion 3 is held in the hardness changing portion 14, the leaf springs 14a and 14b are bent by an outer circumference of the distal end 3a of the insertion portion 3. In FIGS. 5 to 9, a duodenum 104 in the body cavity is shown. A denotes a duodenal papilla and B denotes a choledoch. A biliary tract (not shown) is caused to communicate with this choledoch B.

Next, operation for leading the insertion portion 3 of the cholangioscope 1 to the choledoch B or the like through the duodenum 104 per os using the medical tube 11 having such a configuration is explained.

First, as indicated by an arrow in FIG. 1, the insertion portion 3 of the cholangioscope 1 is inserted through the conduit 13a of the medical tube 11 from the fixing section 12 side. Both the leaf springs 14a and 14b of the hardness changing portion 14 of a spring mouth shape provided at the distal end of the tube main body 13 of the medical tube 11 are bent in directions away from each other by pinching the hinges 14c with fingers. The distal end 3a of the insertion portion 3 of the cholangioscope 1 is faced to the bent leaf springs 14a and 14b. When pressing force applied to both the leaf springs 14a and 14b is released, as shown in FIG. 2A, the leaf springs 14a and 14b nip the distal end 3a of the insertion portion 3 with the resilient force of the leaf springs 14a and 14b. The fixing section 12 provided on a base side of the medical tube 11 is fit in the operation section 2 of the cholangioscope 1 and fixed.

As a result, the medical tube 11 is integrated with the cholangioscope 1. When the bending portion 4 provided in the insertion portion 3 of the cholangioscope 1 is bent, the distal end side of the tube main body 13 of the medical tube 11 is also bent in the same direction.

Figure 5:
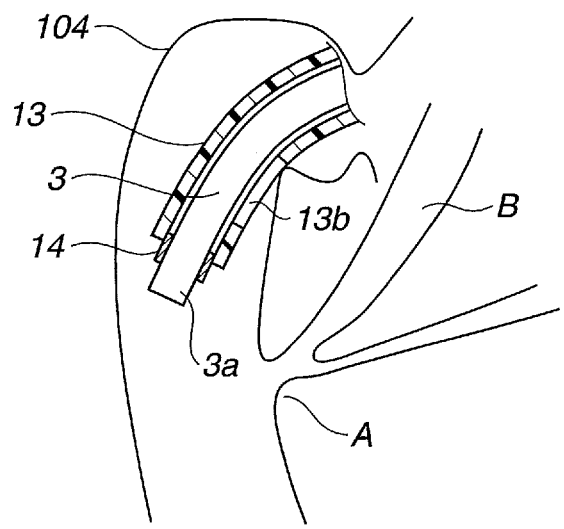
Figure 6:
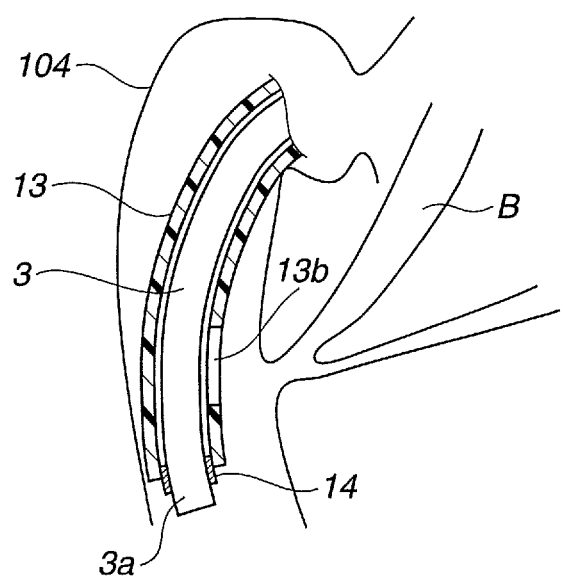
Figure 7:
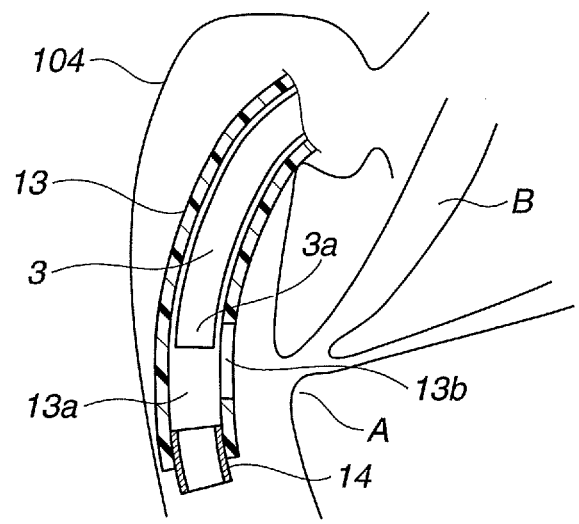

Subsequently, the insertion portion 3 of the cholangioscope 1 is inserted into a subject per os together with the tube main body 13 of the medical tube 11. As shown in FIG. 5, the distal end 3a of the insertion portion 3 is led to the duodenum 104 under the observation by the cholangioscope 1. As shown in FIG. 6, when the side hole 13b opened on the outer circumferential side of the tube main body 13 provided in the medical tube 11 reaches near the duodenal papilla A, the insertion operation for the cholangioscope 1 is stopped and the insertion portion 3 of the cholangioscope 1 is retracted from the conduit 13a of the medical tube 11. Then, as shown in FIG. 7, the distal end 3a of the insertion portion 3 slips off from between the leaf springs 14a and 14b of the hardness changing portion 14, which nip this distal end 3a, and retracts.

Figure 3B:
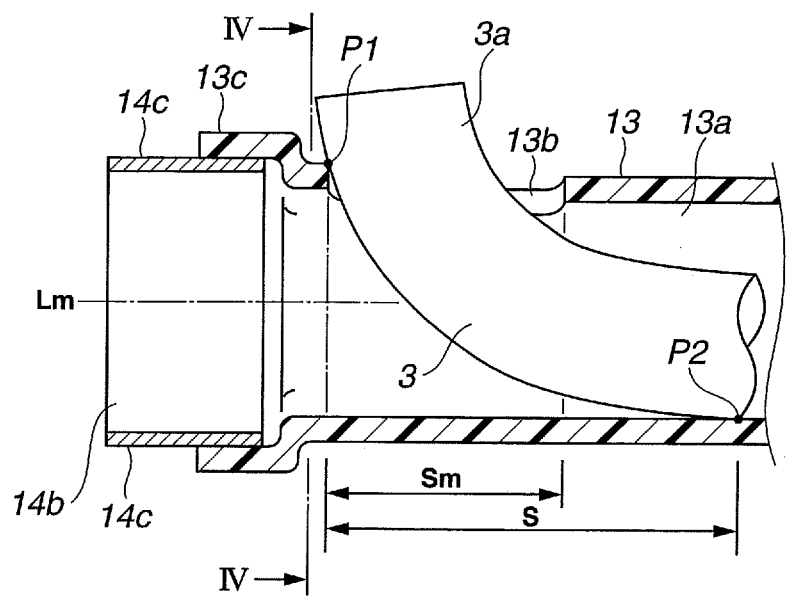
FIG. 3B is a main part right side sectional view of FIG. 3A.
Figure 4:
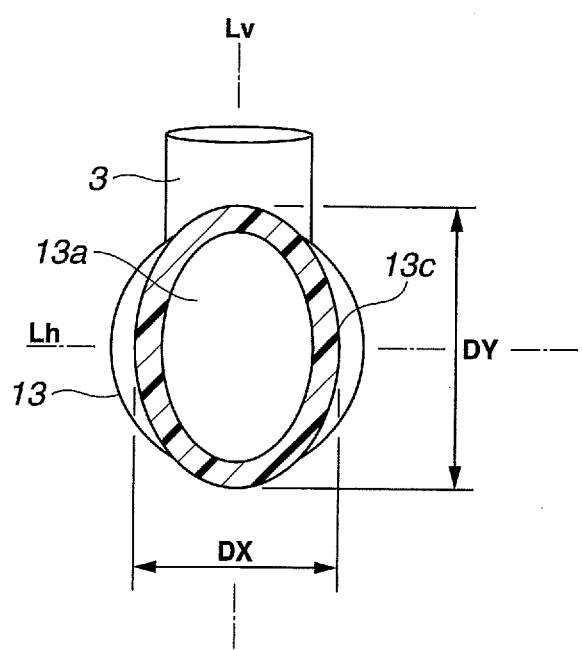

As a result, as shown in FIGS. 3A and 3B, both the leaf springs 14a and 14b of the hardness changing portion 14 close. The distal end portion 13c of the tube main body 13 is elastically deformed to be slim in a straight line shape in a direction in which the side hole 13b and a side opposed to this side hole 13b across a major axis (the axis of the conduit 13a) Lm are connected (this direction is hereinafter referred to as "vertical axis Lv" for convenience of explanation). When the distal end portion 13c of the tube main body 13 is elastically deformed to be slim in a straight line shape, as shown in FIG. 4, in the distal end portion 13c of the tube main body 13, a sectional shape from a region where the hardness changing portion 14 is provided to a predetermined range in the back changes in the vertical axis Lv direction and a direction passing through the major axis Lm and orthogonal to the vertical axis Lv (this direction is hereinafter referred to as "horizontal axis Lh" for convenience of explanation). When width in the vertical axis Lv direction is represented as DY and width in the horizontal axis Lh direction is represented as DX, magnitude relation becomes DY>DX. The distal end portion 13c is deformed to be long in a direction in which the side hole 13b is formed.

As the sectional shape on the distal end portion 13c side of the tube main body 13, the width DY in the vertical axis Lv direction is set larger than the width DX of the vertical axis Lh, in other words, the width DX of the horizontal axis Lh is set smaller than the width DY in the vertical axis Lv direction, whereby a modulus of section of the vertical axis Lv increases and the distal end portion 13c of the tube main body 13 is less easily bent in the vertical axis Lv direction.

Figure 8:
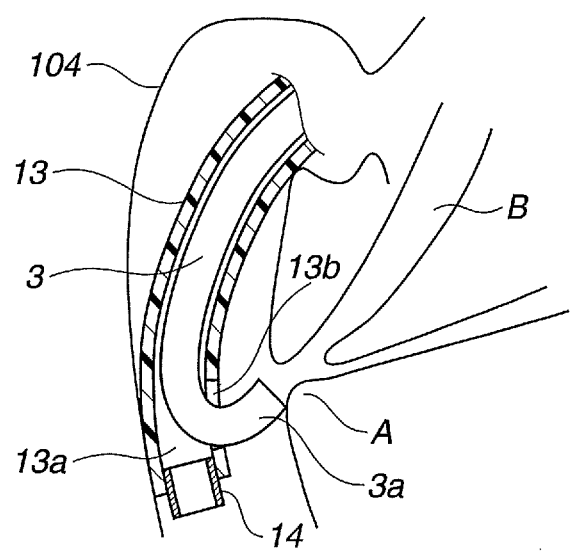

Thereafter, as shown in FIG. 8, the bending portion 4 provided in the insertion portion 3 of the cholangioscope 1 is bent and the distal end 3a is projected from the side hole 13b opened in the tube main body 13. This distal end 3a is further bent at an acute angle and faced to the duodenal papilla A. There is a limit in a bending amount of the bending portion 4 itself. It is difficult to bend, only with the bending of this bending portion 4, the distal end 3a at an acute angle to a state shown in FIG. 8. As shown in FIG. 3B, the insertion portion 3 is bent toward the side hole 13b, whereby the insertion portion 3 is bent while being supported by a distal end side edge portion P1 of the side hole 13b and a region (a conduit supporting portion) P2 set in contact with the inner surface of the conduit 13a. The distal end side edge portion P1 is pressed by the reaction of the insertion portion 3 in a direction for resetting the bending (the counterclockwise direction in FIG. 3B) with the conduit supporting portion P2 as a fulcrum.

Figure 9:
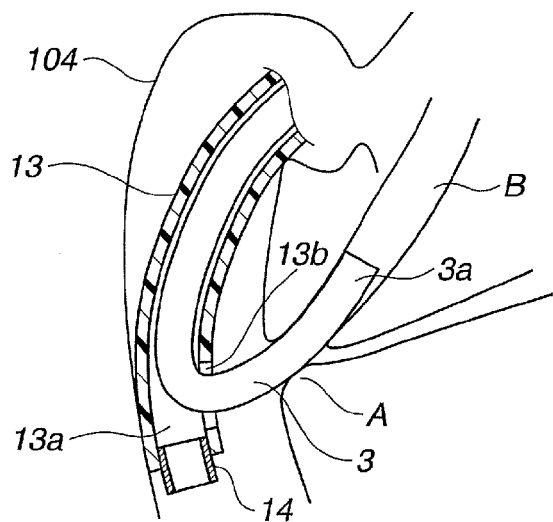

However, as explained above, the tube main body 13 is elastically deformed to be long in the direction in which the side hole 13b is opened (the vertical axis Lv) and the modulus of section of the vertical axis Lv is large. Therefore, even if the insertion portion 3 of the cholangioscope 1 is bent with the distal end side edge portion P1 as a fulcrum, the distal end portion 13c of the tube main body 13 is less easily bent in the vertical axis Lv direction. As a result, an advancing direction of the distal end 3a of the insertion portion 3 can be accurately changed toward the duodenal papilla A. As shown in FIG. 9, the insertion portion 3 of the cholangioscope 1 can be easily led in the direction of the choledoch B through the duodenal papilla A. Therefore, operability is high.

As explained above, in the present embodiment, the hardness changing portion 14 of a spring mouth shape is provided at the distal end portion 13c of the tube main body 13 of the medical tube 11. When the insertion portion 3 of the cholangioscope 1 is inserted into the duodenum 104 per os, the hardness changing portion 14 is caused to nip the distal end 3a of the insertion portion 3 provided in the cholangioscope 1, whereby the distal end portion 13c of the tube main body 13 is formed in a substantially circular shape. Therefore, flexibility of the tube main body 13 is maintained and insertability into the body cavity can be secured. When the insertion portion 3 of the cholangioscope 1 is projected in a state in which the insertion portion 3 is inserted through the side hole 13b of the tube main body 13 and bent, since the tube main body 13 is elastically deformed to be slim in the direction of the vertical axis Lv, the modulus of section on the vertical axis Lv side increases and the insertion portion 3 is less easily bent in the direction of the vertical axis Lv. As a result, it is possible to realize simplification of the structure without structurally setting the rigidity around the side hole 13b high. Therefore, in the present embodiment, the insertion portion 3 functions as an operation section for operating the hardness changing portion 14.

The tube main body 13 of the medical tube 11 has a portion on the distal end side elastically deformed (the hardness of which is changed) by the operation of the hardness changing portion 14 and a portion on the rear end side not elastically deformed (the hardness of which is not changed) even if the hardness changing portion 14 operates. As shown in FIG. 3B, a range of the portion on the distal end side includes a region S from the distal end side edge portion P1 of the side hole 13b to the conduit supporting portion P2. More specifically, a distal end side from the conduit supporting portion P2 is the portion on the distal end side and a rear end side from the conduit supporting portion P2 is the portion on the rear end side. However, actually, since the distal end portion 13c to which the hardness changing portion 14 is attached is also elastically deformed, a region from the distal end of the tube main body 13 to the conduit supporting portion P2 is a region where hardness is changed.

Figure 10:
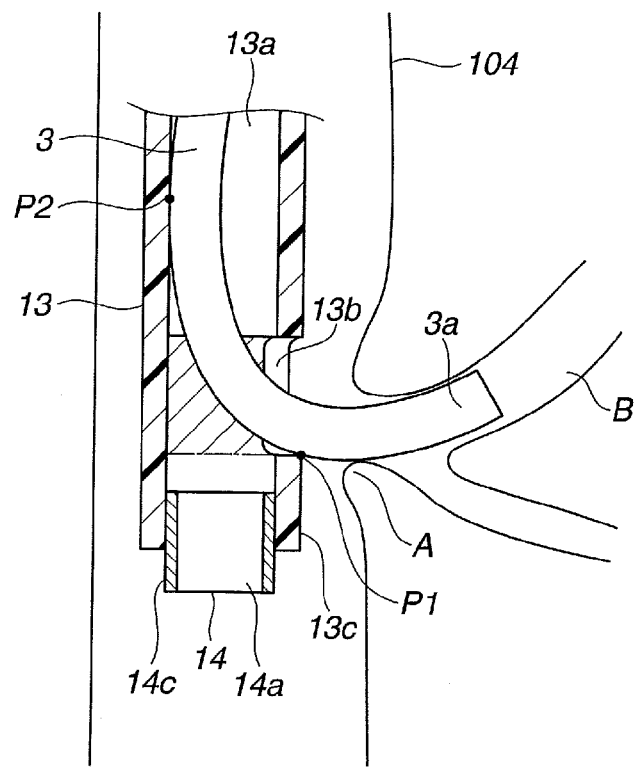

As indicated by hatching in FIG. 10, the rigidity of the outer circumferential side surface on which the side hole 13b of the tube main body 13 is opened is reduced by the opening of this side hole 13b. Therefore, if at least this outer circumferential side surface is elastically deformed to increase the modulus of section in the vertical axis Lv direction, it is possible to secure rigidity at the time when the distal end 3a of the insertion portion 3 of the cholangioscope 1 is projected from the side hole 13b.

Second Embodiment

A second embodiment of the present invention is shown in FIGS. 11 to 16. Components same as those in the first embodiment are denoted by the same reference numerals and signs and explanation of the components is omitted.

In the first embodiment explained above, the hardness changing portion 14 of a spring mouth shape is provided at the distal end portion 13c of the tube main body 13 provided in the medical tube 11. The region from the distal end of the tube main body 13 to the conduit supporting portion P2 is elastically deformed by the hardness changing portion 14. However, in the present embodiment, the tube main body 13 includes a side wire 21 as a hardness changing portion having a small diameter. At least the region S (see FIG. 3) of the tube main body 13 is elastically deformed by pulling this side wire 21.

Figure 11:
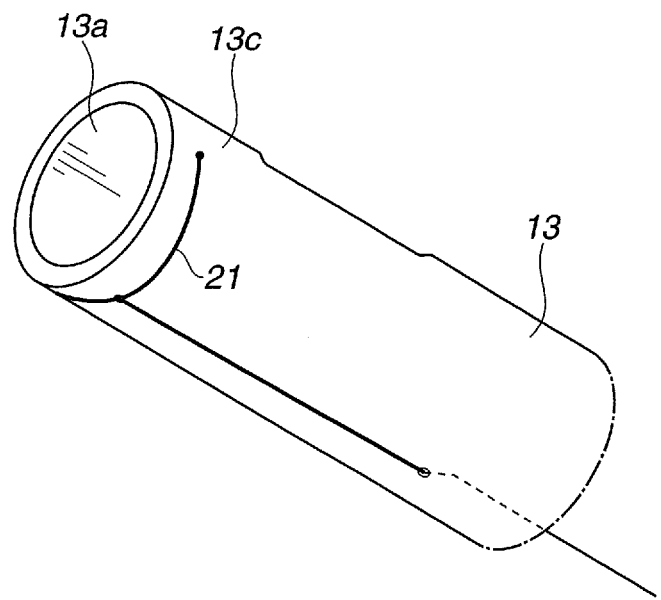
Figure 12A:
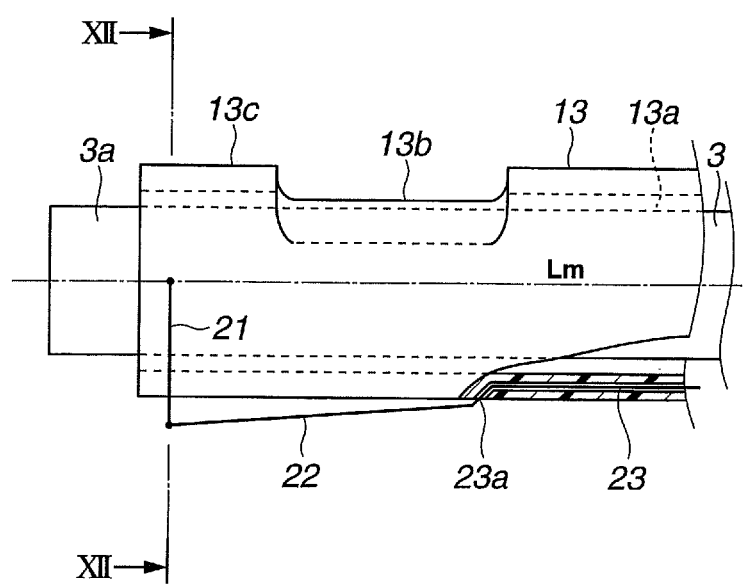
FIG. 12A is a side view of the distal end portion of the medical tube.
Figure 12B:
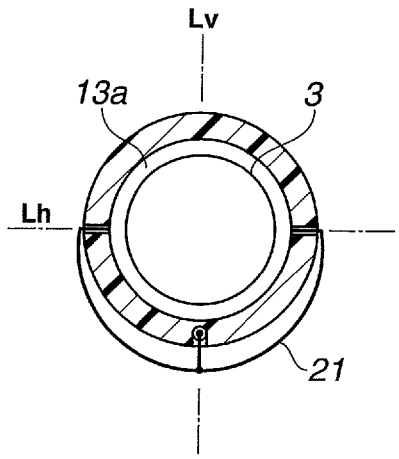
FIG. 12B is a XII-XII sectional view of FIG. 12A.

Specifically, as shown in FIGS. 11 and 12A, the side wire 21 is disposed at the distal end portion 3c of the tube main body 13 of the medical tube 11. Both ends of this side wire 21 are fixed to a position further in the front than the distal end side edge portion P1 of the side hole 13b where the horizontal axis Lh passes. In a loosened state, this side wire 21 is disposed, with respect to the outer circumferential side of the distal end portion 13c, on the opposite side of the surface in which the side hole 13b is opened.

One end of an operation wire 22 is tied to a center of this side wire 21. This operation wire 22 is inserted through a wire lumen 23 formed in a thick portion of the tube main body 13. The wire lumen 23 is formed along the major axis Lm in the thick portion on a side opposed to the side hole 13b of the tube main body 13 across the major axis Lm. A wire projection port 23a is opened on an outer circumferential side slightly behind a position corresponding to the conduit supporting portion P2.

Figure 13:
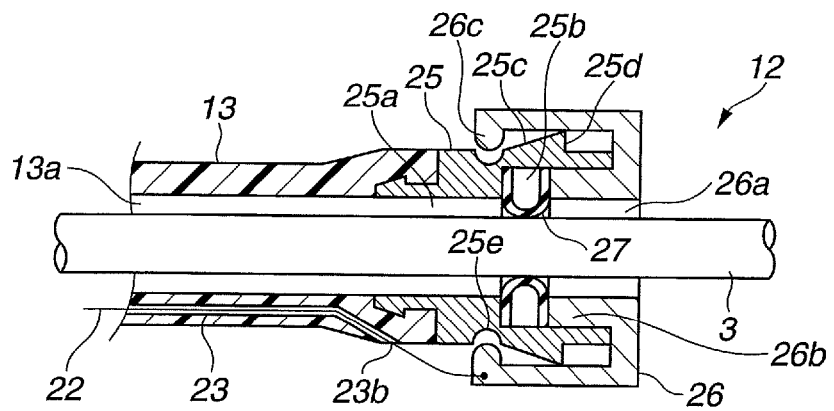

As shown in FIG. 13, an insertion portion fixing mechanism for fixing a proximal end side of the insertion portion 3 of the cholangioscope 1 is provided in the fixing section 12 provided on the base side of the medical tube 11. This fixing section 12 includes a pipe sleeve 25 fixedly provided at the rear end of the tube main body 13, a stopper ring 26 sheathed over this pipe sleeve 25, and a tightening member 27 provided between the pipe sleeve 25 and the stopper ring 26. Conduits 25a and 26a that communicate with the conduit 13a formed in the tube main body 13 are respectively opened in centers of the pipe sleeve 25 and the stopper ring 26.

A wire insertion port 23b of the wire lumen 23 is opened on the outer circumferential side on the base side of this tube main body 13. A distal end of the operation wire 22 is inserted through the wire lumen 23 from the wire insertion port 23b, projected from the wire projection port 23a opened at the distal end side, and tied to the side wire 21. A rear end of the operation wire 22 is fixed to the stopper ring 26.

A recess 25b is formed at a rear end of the pipe sleeve 25. The tightening member 27 as a component of the insertion portion fixing mechanism is fit in this recess 25b. This tightening member 27 is a ring member having elasticity such as rubber and is formed in a U shape in section opening outward. Further, a projection 26b projected to the center of the stopper ring 26 is fit in the recess 25b to freely advance and retract.

The tightening member 27 is pressed and separated at the distal end of the projection 26b according to the advancing and retracting action of the stopper ring 26. When the tightening member 27 is pressed, an inner circumference thereof is reduced in diameter. When the tightening member 27 is separated, the inner circumference is expanded in diameter. In a state in which the tightening member 27 is reduced in diameter, the insertion portion 3 of the cholangioscope 1 is tightened and fixed. When the inner circumference of this tightening member 27 is expanded in diameter, the fixing of the insertion portion 3 is released.

A taper guide 25c expanded in diameter from a distal end side to a rear end side is formed on an outer circumference of the pipe sleeve 25. A locking step portion 25d is formed at the rear end of this taper guide 25c. A stopper portion 26c formed at an opening end edge of the stopper ring 26 is set in slide contact with this taper guide 25c. An annular groove 26e to which an inner circumference of the stopper portion 26c is locked is formed on the distal end side of the taper guide 25c.

In a state in which the inner circumference of the stopper portion 26c is engaged with the annular groove 26e, the projection 26b of the stopper ring 26 compresses the tightening member 27. As shown in FIG. 13, the tightening member 27 tightens and fixes the insertion portion 3 of the cholangioscope 1 inserted through the conduit 25a. On the other hand, when the stopper ring 26 is pulled, the stopper portion 26c slides on the taper guide 25c and at least one of the stopper portion 26c and the taper guide 25c is elastically deformed and movement of the stopper portion 26c is allowed.

When the stopper portion 26c climbs over the taper guide 25c and is locked to the locking step portion 25d, this pulled state is maintained. In a state in which the stopper portion 26c of the stopper ring 26 is locked to the locking step portion 25d, the operation wire 22, the rear end of which is fixed to this stopper ring 26, is pulled, the side wire 21 fixedly provided on the distal end side of the tube main body 13 is pulled, and the outer circumferential side on the horizontal axis Lh side of the distal end portion 13c of the tube main body 13 is pressed by this side wire 21.

Next, actions of the present embodiment are explained. As shown in FIGS. 12A and 13, in an initial state in which the insertion portion 3 of the cholangioscope 1 is inserted in the conduits 13a, 25a, and 26a of the medical tube 11, the distal end portion 13c of the insertion portion 3 is slightly projected from the distal end portion 13c of the tube main body 13 and the inner circumference of the stopper portion 26c formed in the stopper ring 26 of the fixing section 12 is locked to the annular groove 26e formed on the outer circumference of the pipe sleeve 25.

In a state in which the stopper portion 26c of the stopper ring 26 is locked to an annular groove 25e of the pipe sleeve 25, the tightening member 27 housed in the recess 25b of the pipe sleeve 25 is compressed between the bottom of the recess 25b and the projection 26b formed in the stopper ring 26. As a result, an inner circumference of the tightening member 27 is swelled in an axis center direction. An outer circumference of the insertion portion 3 is tightened by this swelling and the medical tube 11 is fixed to the insertion portion 3.

Subsequently, the insertion portion 3 of the cholangioscope 1 is inserted into a subject per os together with the tube main body 13 of the medical tube 11. The distal end 3a of the insertion portion 3 is led to the duodenum 104 under the observation by the cholangioscope 1. When the distal end 3a is led to the duodenum 104, since the base side of the medical tube 11 is fixed to the insertion portion 3 by the tightening member 27, the insertion portion 3 and the tube main body 13 of the medical tube 11 can be integrally moved in the body cavity.

Figure 14:
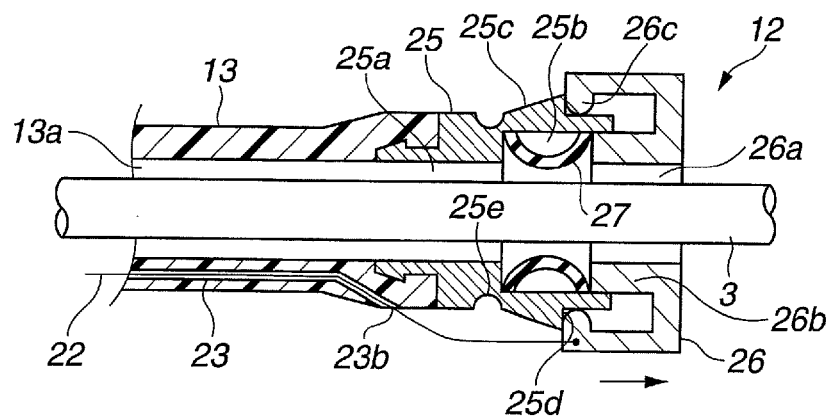

When the side hole 13b of the tube main body 13 reaches near the duodenal papilla A, the insertion operation for the cholangioscope 1 is stopped and the stopper ring 26 provided in the fixing section 12 of the medical tube 11 is pulled. The stopper portion 26c formed in this stopper ring 26 is disengaged from the annular groove 26e formed in the pipe sleeve 25. As shown in FIG. 14, the stopper portion 26c is locked to the locking step portion 25d formed on the base side of the pipe sleeve 25.

Then, the pressing of the projection 26b provided in the stopper ring 26 against the tightening member 27 is released and the insertion portion 3 of the cholangioscope 1 can move relative to the medical tube 11. At the same time, the operation wire 22, the rear end of which is fixed to the stopper ring 26, is pulled.

Figure 15:
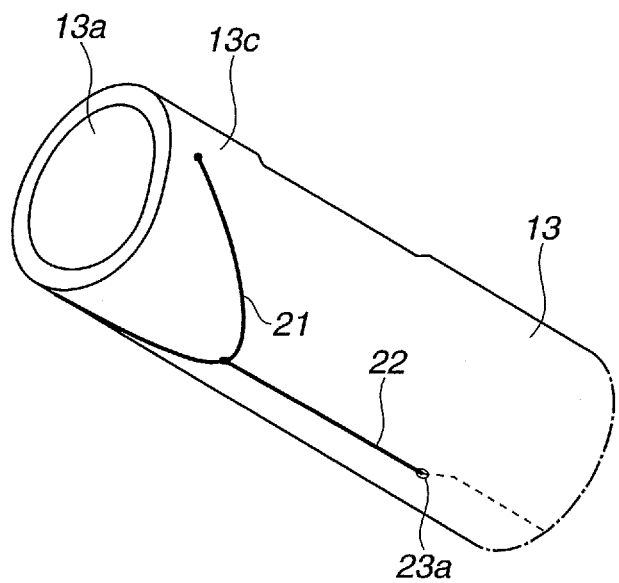
Figure 16A:
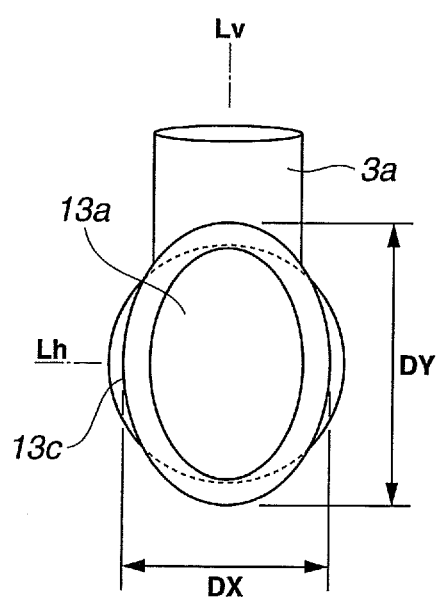
FIG. 16A is a front view of a state in which a distal end of an endoscope is projected from a side hole of the tube main body.
Figure 16B:
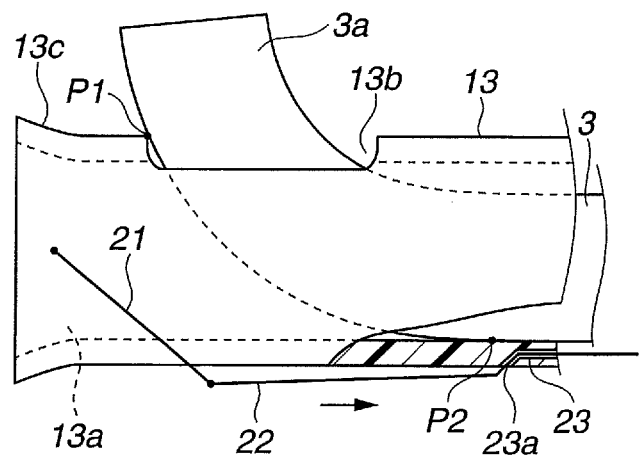

When the operation wire 22 is pulled, as shown in FIGS. 15 and 16A, the side wire 21 tied to the distal end of this operation wire 22 is pulled. Then, this side wire 21 is straightened between a fixed position at the distal end thereof and the wire projection port 23a of the wire lumen 23 and force is applied in the major axis Lm direction. Therefore, the horizontal axis Lh direction of the distal end portion 13c is pressed.

Thereafter, the insertion portion 3 of the cholangioscope 1 is retracted from the medical tube 11, the bending portion 4 (see FIG. 1) of the insertion portion 3 is bent by bending operation, and the distal end 3a is directed in the side hole 13b direction. At this point, since the horizontal axis Lh direction of the distal end portion 13c of the tube main body 13 is compressed by force acting on the major axis Lm of the side wire 21, at least from the distal end portion 13c to the rear side of the side hole 13b, the width DX in the horizontal axis Lh direction is pressed and deformed to be short and the width DY in the vertical axis Lv direction is relatively long. Therefore, the modulus of section in the vertical axis Lv direction increases and the distal end portion 13c is less easily bent in the vertical axis Lv direction. As a result, it is possible to bend the insertion portion 3 of the cholangioscope 1 with the distal end side edge portion P1 of the side hole 13b as a fulcrum and accurately change the advancing direction toward the duodenal papilla A.

In the present embodiment, the release of the fixing of the medical tube 11 to the insertion portion 3 and the pressing and deformation of the distal end portion 13c of the tube main body 13 are simultaneously performed according to the advancing and retracting motion of the stopper ring 26. Therefore, operability is high.

Third Embodiment

Figure 17:
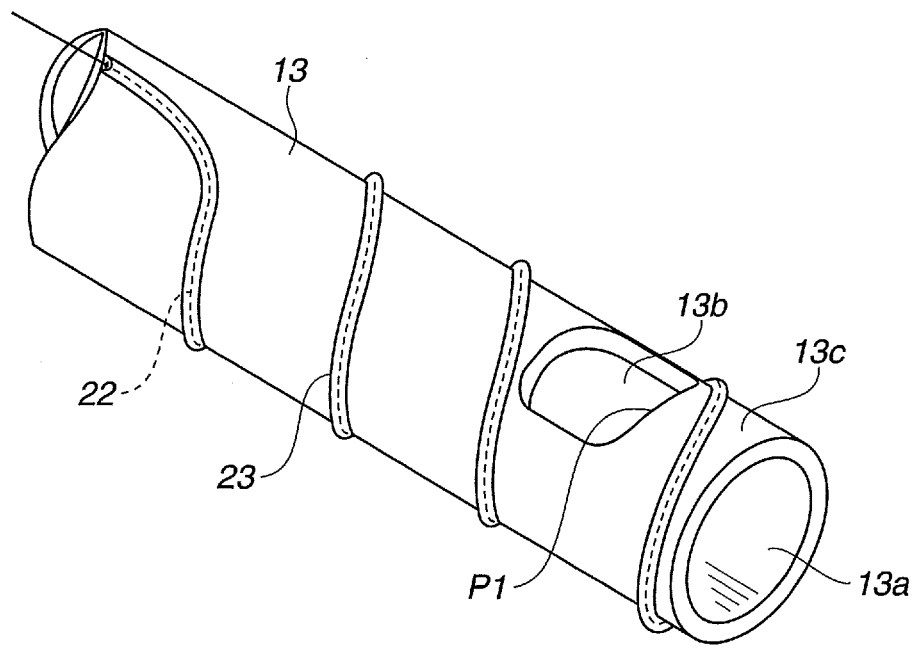
FIG. 17 is a main part perspective view of a medical tube according to a third embodiment of the present invention.

A main part perspective view of a medical tube according to a third embodiment of the present invention is shown in FIG. 17. The present embodiment is a modification of the second embodiment explained above. The tube main body 13 adopted in the present embodiment is adopted instead of the tube main body 13 adopted in the second embodiment. The structure on the rear end side of the tube main body 13 is the same as that shown in FIGS. 13 and 14. Therefore, the structure on the rear end side of the tube main body 13 is explained with reference to FIGS. 13 and 14. Components same as those in the second embodiment are denoted by the same reference numerals and signs and explained.

In the second embodiment, the side wire 21 is coupled to the distal end portion 13c of the tube main body 13. At least the region from the distal end portion 13c of the tube main body 13 to the distal end side edge portion P1 is elastically deformed by pulling this side wire 21. However, in the present embodiment, the operation wire 22 is wound on the distal end portion 13c side of the tube main body 13 and the distal end portion 13c is elastically deformed by pulling the operation wire 22.

Specifically, on the outer circumferential side surface of the tube main body 13, from the distal end portion 13c to at least near the conduit supporting portion P2, the wire lumen 23 is formed in a spiral shape along the major axis Lm direction of the tube main body 13. A user's hand side of the tube main body 13 has a structure same as that shown in FIGS. 13 and 14 in the second embodiment.

The distal end of the operation wire 22 inserted through this wire lumen 23 is fixed to the distal end of the tube main body 13. The rear end of the operation wire 22 is fixed to the stopper ring 26 fixed on the user's hand side of the tube main body 13 (see FIGS. 13 and 14).

In such a configuration, as in the second embodiment, in a state in which the stopper portion 26c provided in the stopper ring 26 is locked to the annular groove 25e formed in the pipe sleeve 25, the operation wire 22 is coupled to the stopper ring 26 in a slightly loosened state. Therefore, the flexibility is maintained on the distal end portion 13c side of the tube main body 13.

As shown in FIG. 14, when the stopper portion 26c formed in the stopper ring 26 is disengaged from the annular groove 25e formed in the pipe sleeve 25 and is locked to the locking step portion 25 formed on the base side of the pipe sleeve 25, the operation wire 22 is pulled.

When this operation wire 22 is pulled, since the wire lumen 23 on the distal end side is formed in a spiral shape, the operation wire 22 inserted through the spiral wire lumen 23 is closely attached to the tube main body 13 and the tube main body 13 is tightened. As a result, because of the tightening by this operation wire 22, a region from at least the distal end of the tube main body 13 to near the conduit supporting portion P2 is less easily bent and apparent hardness is increased (apparently hardened). Therefore, in the present embodiment, the distal end side of the operation wire 22 inserted through the spiral wire lumen 23 functions as the harness changing portion.

As a result, when the insertion portion 3 of the cholangioscope 1 inserted through the conduit 13a of this tube main body 13 is bent and the distal end 3a is projected from the side hole 13b of the tube main body 13, even if the distal end side edge portion P1 is pressed by this distal end 3a, the tube main body 13 is less easily bent and an advancing direction of the insertion portion 3 can be accurately led in the choledoch B (see FIG. 8) direction with the distal end side edge portion P1 of the side hole 13b as a fulcrum.

Fourth Embodiment

A fourth embodiment of the present invention is shown in FIGS. 18A to 22B. Components same as those in the second embodiment explained above are denoted by the same reference numerals and signs and explanation of the components is omitted.

In the second and third embodiments explained above, the distal end side of the tube main body 13 is deformed or tightened by the mechanical link operation of the operation wire 22 to change the hardness on the distal end portion 13c side of the tube main body 13. However, in the present embodiment, a core member 32 as a hardness changing portion is provided on the distal end portion 13c side of the tube main body 13. This core member 32 is electrically actuated to change the hardness.

Specifically, in the present embodiment, a hardness changing chamber 31 is formed in a region of the distal end portion 13c of the tube main body 13 of the medical tube 11 opposed to the side hole 13b across the major axis Lm. The core member 32 is inserted through this hardness changing chamber 31.

Figure 20A:
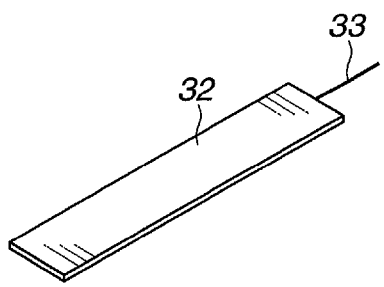
FIG. 20A is a perspective view before deformation of a core member.
Figure 20B:
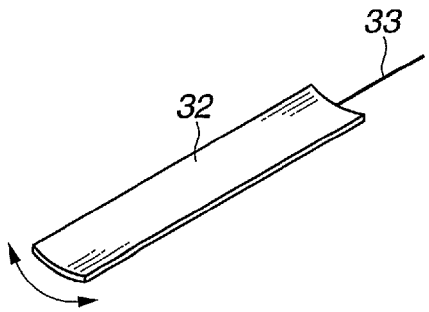
FIG. 20B is a perspective view after the deformation of the core member.

This core member 32 is a member obtained by processing a shape memory member having conductivity such as a shape memory alloy or shape memory resin to be formed as a slim flat member having flexibility. As shown in FIG. 20A, during non-energization, the core member 32 maintains the flat shape and has the flexibility in a longitudinal direction. However, as shown in FIG. 20B, when energized, the core member 32 is deformed to be bent in a shape stored in advance, i.e., in a direction orthogonal to the longitudinal direction and the modulus of section in the longitudinal direction increases.

Figure 18A:
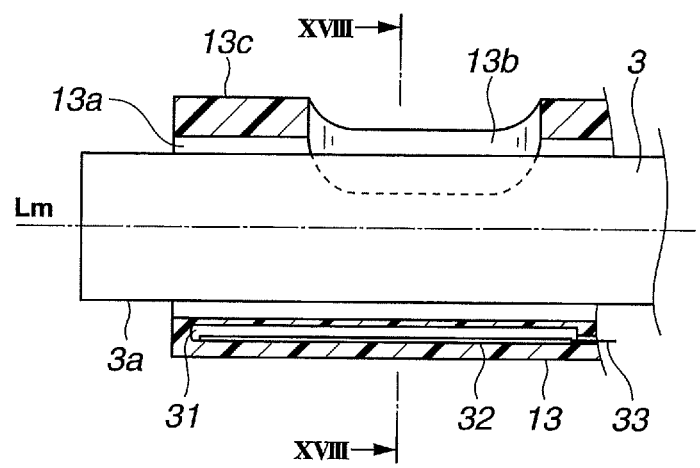
Figure 18B:
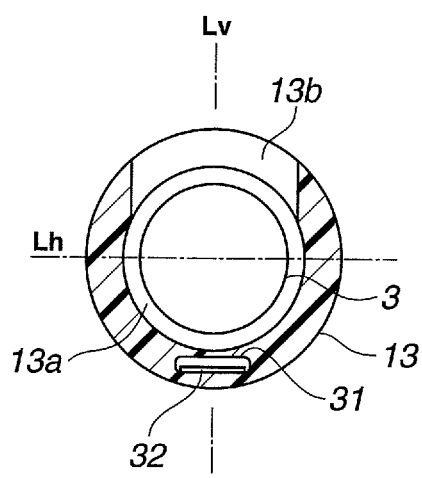
FIG. 18B is a XVIII-XVIII sectional view of FIG. 18A.

One end of a lead wire 33 is electrically connected to a rear end of this core member 32. Although not shown in the figure, a distal end of the core member 32 is grounded in a predetermined manner. As shown in FIG. 18A, this lead wire 33 passes through the thickness of the tube main body 13 and is extended out to the rear end side.

Figure 19:
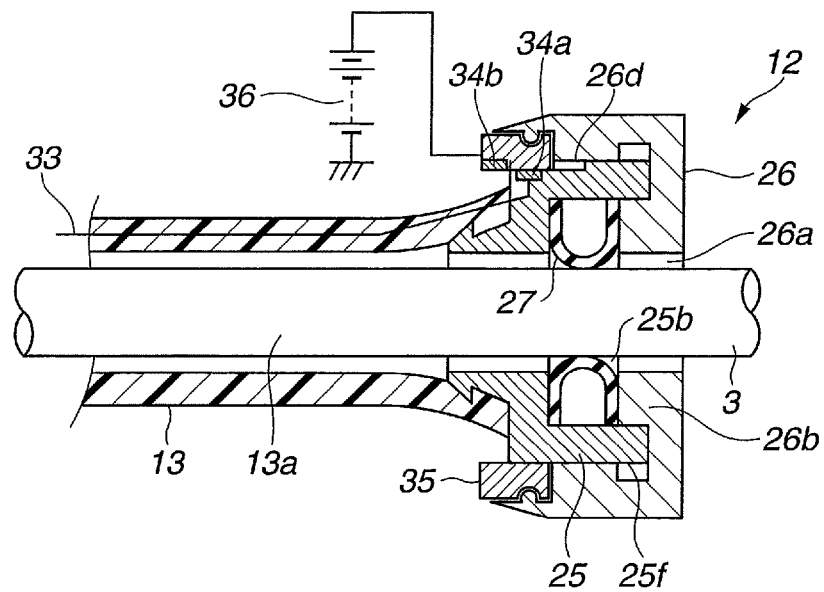

As shown in FIG. 19, a fixed contact point 34a is provided on the outer circumference of the pipe sleeve 25 provided in the fixing section 12 fixedly provided at the rear end of the tube main body 13. The pipe sleeve 25 according to the present embodiment is formed of an insulative material such as a rigid resin material. The rear end of the lead wire 33 is electrically connected to this fixed contact point 34a. A guide surface 25f is formed at an outer circumferential end of this pipe sleeve 25. A sliding surface 26d formed on the inner circumference of the stopper ring 26 is set in slide contact with this guide surface 25f. Further, an insulating collar 35 is fixedly provided at the distal end on the inner circumference of this stopper ring 26. A movable contact point 34b is fixedly provided on an inner circumference of this insulating collar 35. The guide surface 25f and the sliding surface 26d are allowed to move only in an axis length direction by spline engagement or the like. The movable contact point 34b is disposed in a position corresponding to the fixed contact point 34a.

As shown in FIG. 19, in a state in which the rear end side inner surface of the stopper ring 26 is set in contact with the rear end surface of the pipe sleeve 25, the projection 26b formed in this stopper ring 26 presses the tightening member 27 as the component of the insertion portion fixing mechanism. The tightening member 27 tightens the outer circumferential side of the insertion portion 3 of the cholangioscope 1. In this state, a state of the movable contact point 34b and the fixed contact point 34a is an OFF state in which the movable contact point 34b deviates from the fixed contact point 34a.

Figure 21:
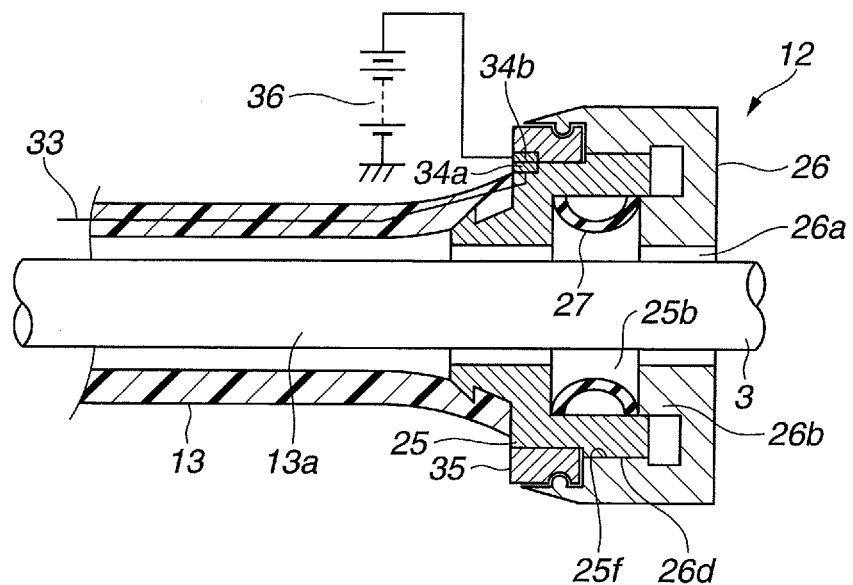

On the other hand, as shown in FIG. 21, when the stopper ring 26 is pulled, the pressing of the tightening member 27 by the projection 26b is released, the movable contact point 34b and the fixed contact point 34a are brought into contact with each other, and the state changes to an ON state. A power supply 36 is connected to this movable contact point 34b. In the ON state in which both the contact points 34a and 34b are conducted, electric power is supplied to the core member 32 via the lead wire 33.

In such a configuration, as shown in FIG. 19, in a state in which the rear end side inner surface of the stopper ring 26 is set in contact with the rear end of the pipe sleeve 25, since the projection 26b presses the tightening member 27, the insertion portion 3 of the cholangioscope 1 is tightened and fixed by this tightening member 27. In this state, a state of the movable contact point 34b and the fixed contact point 34a is the OFF state in which the movable contact point 34b is separated from the fixed contact point 34a. Therefore, the core member 32 housed in the hardness changing chamber 31 provided on the distal end side of the tube main body 13 maintains the flat state as shown in FIG. 20A. Therefore, the flexibility is maintained on the distal end portion 13c side of the tube main body 13.

On the other hand, as shown in FIG. 21, when the stopper ring 26 is pulled, the pressing of the projection 26b against the tightening member 27 is released and the insertion portion 3 of the cholangioscope 1 can freely move in the conduit 13a formed in the tube main body 13. When the insertion portion 3 moves, the movable contact point 34b fixedly provided in the stopper ring 26 via the insulating collar 35 comes into contact with the fixed contact point 34a fixedly provided in the pipe sleeve 25. Electric power from the power supply 36 is supplied to the core member 32 via the lead wire 33.

Figure 22A:
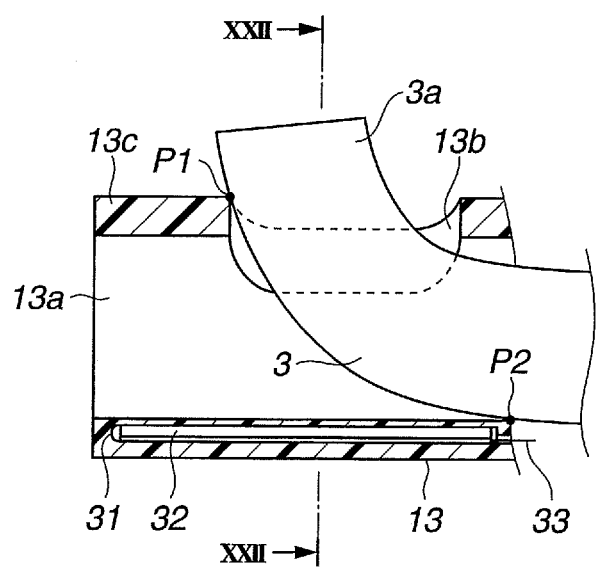
FIG. 22A is a sectional side view equivalent to FIG. 18A of a state in which an insertion portion is projected from a side hole.
Figure 22B:
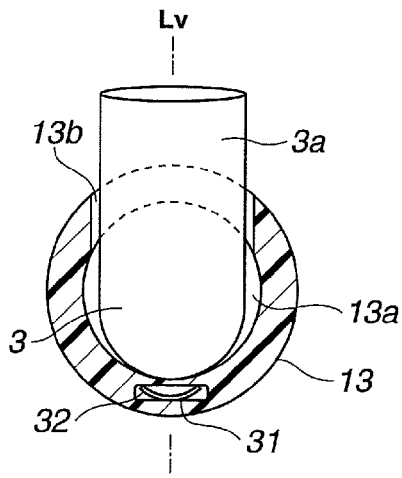
Figure 23A:
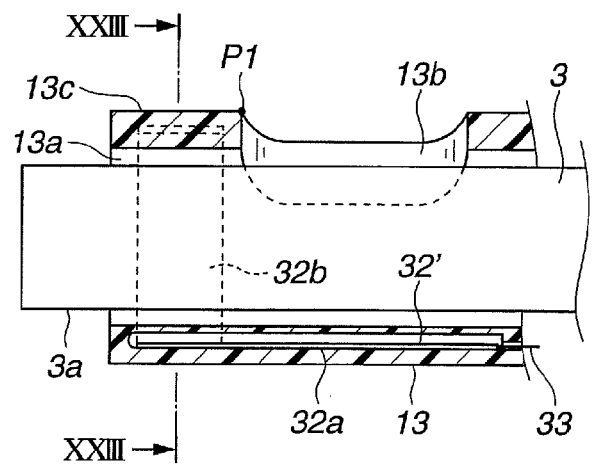
Figure 23B:
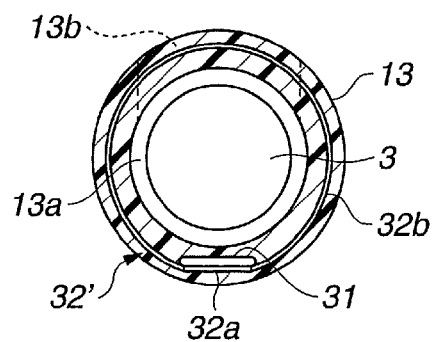
FIG. 23B is a XXIII-XXIII sectional view of FIG. 23A.

Then, the core member 32 generates heat with internal resistance of the core member 32. As shown in FIG. 20B, the core member 32 is bent in a shape stored in advance, i.e., in a direction crossing (in the present embodiment, orthogonal to) the major axis Lm to change a sectional shape thereof, whereby the modulus of section in the major axis Lm direction increases. As shown in FIGS. 22A and 22B, from the distal end portion 13c of the tube main body 13 to near the conduit supporting section P2, rigidity in the vertical axis Lv direction, i.e., with respect to the bending of this tube main body 13 increases. As a result, when the distal end 3a of the insertion portion 3 provided in the cholangioscope 1 is projected from the side hole 13b of the tube main body 13, even if the distal end side edge portion P1 is pressed by this distal end 3a, the tube main body 13 is less easily bent and the advancing direction of the insertion portion 3 can be accurately led in the choledoch B (see FIG. 8) direction with the distal end side edge portion P1 of the side hole 13b as a fulcrum.

As explained above, in the present embodiment, since the core member 32 is disposed on the distal end portion 13c of the tube main body 13 and this core member 32 is energized to increase the hardness, it is unnecessary to mechanically actuate this core member 32. Therefore, it is easy to tie the tube main body 13 and simplify manufacturing and assembly of the tube main body 13. In the present embodiment, a state of power supply to the core member 32 is switched according to the movement of the fixed contact point 34a and the movable contact point 34b. However, for example, the power supply state to the core member 32 may be switched by controlling power supply from the power supply 36 according to the operation of the remote switch 7 provided in the operation section 2 of the cholangioscope 1.

Fifth Embodiment

A fifth embodiment of the present invention is shown in FIGS. 23A to 24B. The present embodiment is a modification of the fourth embodiment explained above. A ring portion 32b is formed at a distal end of a main body portion 32a (equivalent to the core member 32 in the fourth embodiment) of the core member 32'. Other components are the same as those in the fourth embodiment. Therefore, components same as those in the fourth embodiment are denoted by the same reference numerals and signs and explanation of the components is omitted.

The ring portion 32b provided at a distal end of the core member 32' is embedded in the distal end portion 13c of the tube main body 13. A cutout portion 32c is formed in a connecting portion of the ring portion 32b and the main body portion 32a of the core member 32'.

Figure 24A:
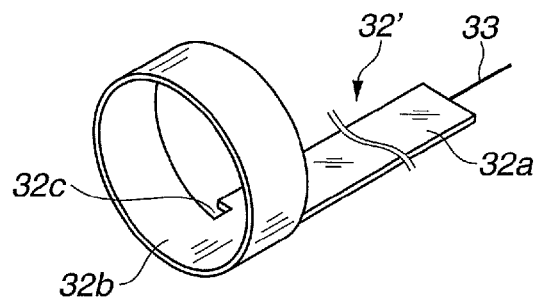
FIG. 24A is a perspective view before deformation of a core member.
Figure 24B:
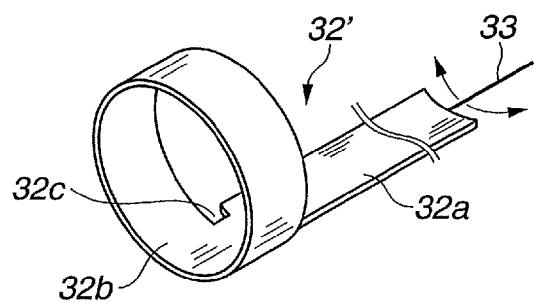

As shown in FIG. 24A, when the core member 32' is not energized by electric power, the cutout portion 32c allows a flat state of the main body portion 32a to be maintained without being restricted by a bent shape of the ring portion 32b. Similarly, as shown in FIG. 24B, when the core member 32' is energized, the main body portion 32a can be displaced without being restricted by the bent shape of the ring portion 32b.

In the present embodiment, since the ring portion 32b is formed at the distal end of the core member 32', the hardness of the distal end portion 13c of the tube main body 13 increases. When the distal end 3a of the insertion portion 3 provided in the cholangioscope 1 is projected from the side hole 13b of the tube main body 13, even if this distal end 3a presses the distal end side edge portion P1, the distal end portion 13c is less easily deformed. The distal end 3a of the insertion portion 3 can be more accurately led in the choledoch B (see FIG. 8) direction with this distal end side edge portion P1 as a fulcrum.

Sixth Embodiment

Figure 25A:
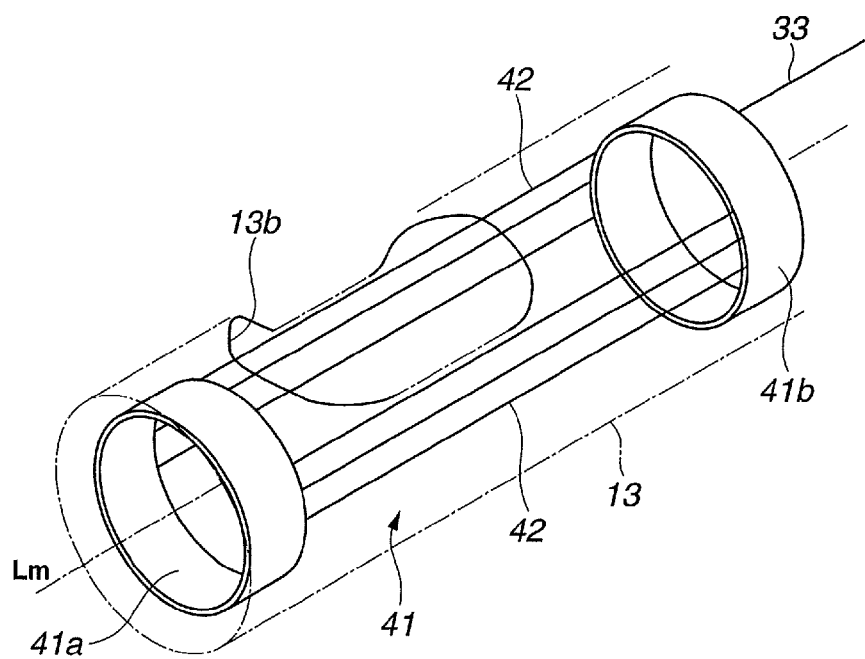
Figure 25B:
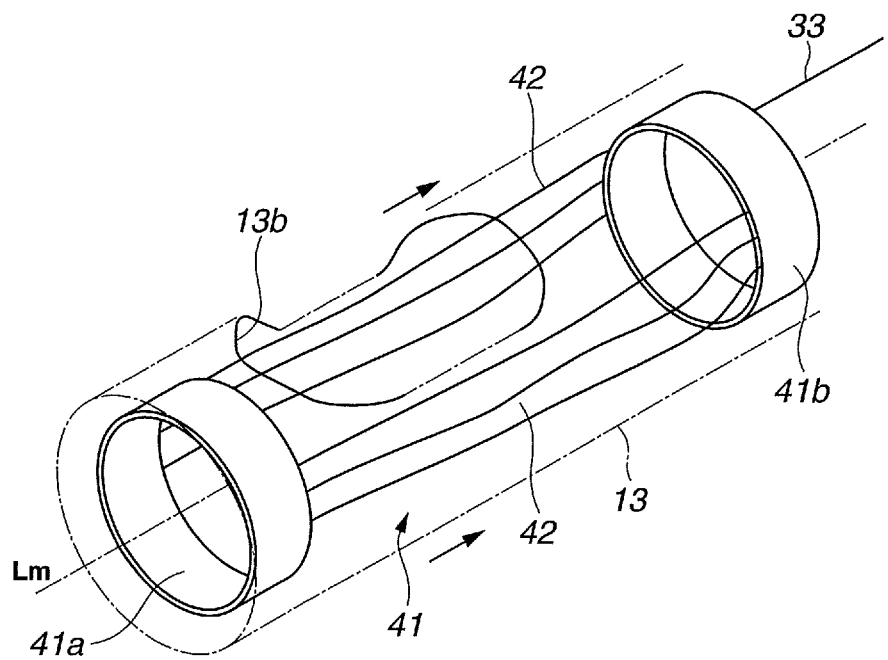
FIG. 25B is a perspective view after the deformation of the hardness changing portion.
Figure 26:
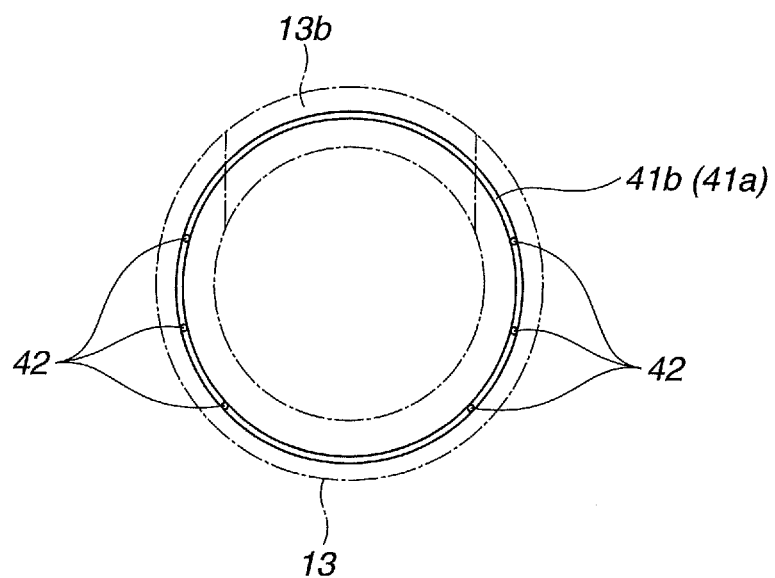
Figure 27:
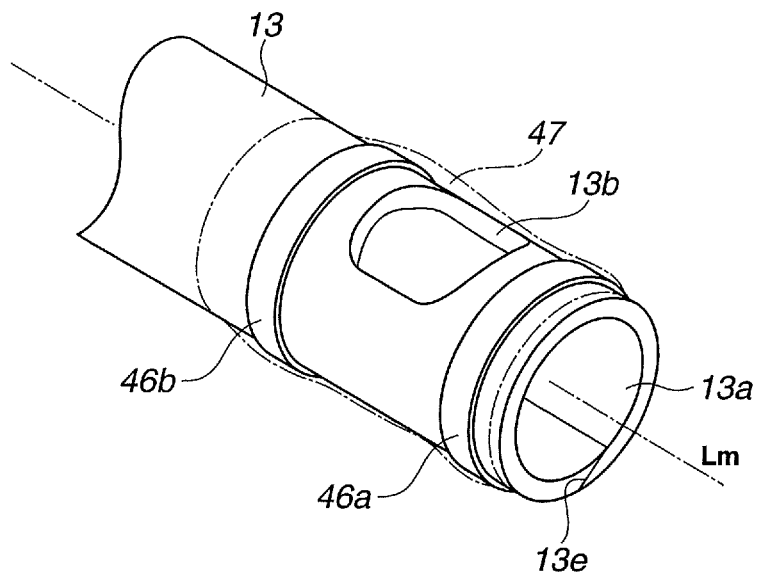
Figure 28:
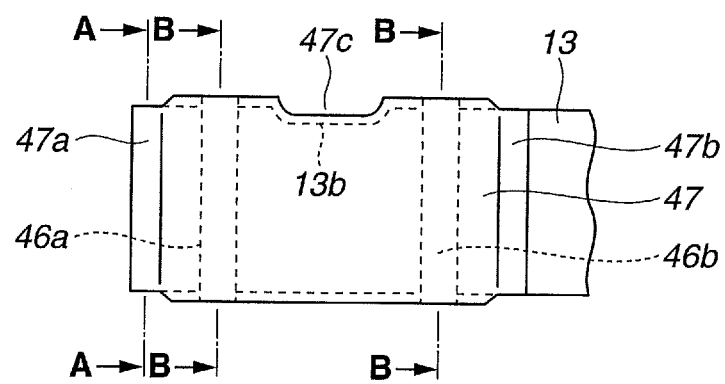

A sixth embodiment of the present invention is shown in FIGS. 25A to 26. Since components on a rear end side of a medical tube are the same as those shown in FIGS. 19 and 21, explanation of the components is omitted.

In the fourth and fifth embodiments explained above, the flat shape memory member is used as the hardness changing portion and the hardness on the distal end portion 13c side of the tube main body 13 is changed according to energization and non-energization to this hardness changing section. However, in the present embodiment, the hardness on the distal end portion 13c of the tube main body 13 is changed by using a linear shape memory member.

Specifically, a hardness changing portion 41 adopted in the present embodiment has a pair of conductive rings 41a and 41b opposed to each other. The conductive rings 41a and 41b are connected by plural wires 42. The conductive ring 41a is grounded, the lead wire 33 is connected to the conductive ring 41b, and this lead wire 33 is connected to the fixed contact point 34a (see FIG. 19) on the proximal end side.

As shown in FIG. 26, in the present embodiment, three wires 42 are disposed on each of sides across the side hole 13b formed in the tube main body 13. The wires 42 are obtained by processing a shape memory member having conductivity. When the wires 42 are energized, the wires 42 are deformed into a shape stored in advance, i.e., a shape bent in a predetermined direction.

Both the conductive rings 41a and 41b are disposed in a front to back direction in which the side hole 13b of the tube main body 13 is placed between the conductive rings 41a and 41b in the major axis Lm direction. Specifically, the conductive ring 41a is inserted on the distal end portion 13c side of the tube main body 13. The other conductive ring 41b is inserted near the conduit supporting portion P2 explained above.

When the wires 42 are in the non-energized state, the wires 42 assume a linear shape and are bent in a bending direction on the distal end portion 13c side of the tube main body 13. On the other hand, when the wires 42 are energized, the wires 42 generate heat with internal resistance of the wires 42 and are about to bend in the shape stored in advance. When the wires 42 bends, as indicated by an arrow in FIG. 25B, the distal end portion 13c of the tube main body 13 is pulled in the rear end direction along the major axis Lm, compressed, and hardened.

As a result, when the distal end 3a (see FIG. 23A) of the insertion portion 3 provided in the cholangioscope 1 is projected from the side hole 13b of the tube main body 13, even if the distal end side edge portion P1 (see FIG. 23A) is pressed by this distal end 3a, the tube main body 13 is less easily bent. The advancing direction of the insertion portion 3 can be accurately led in the choledoch B (see FIG. 8) direction with the distal end side edge portion P1 of the side hole 13b as a fulcrum.

Seventh Embodiment

A seventh embodiment of the present invention is shown in FIGS. 27 to 33B. Since components on a rear end side of a medical tube are the same as those shown in FIGS. 19 and 21, explanation of the components is omitted.

In the third embodiment explained above, the operation wire 22 wound on the distal end portion 13c side of the tube main body 13 is tightened to increase the hardness on the distal end portion 13c side. However, in the present embodiment, loop plates 46a and 46b as a pair of hardness changing portions made of a shape memory member having conductivity are disposed in the front and back across the side hole 13b of the tube main body 13 (the major axis Lm direction). The tube main body 13 is rounded and squeezed by the loop plates 46a and 46b to change the thickness of this tube main body 13 and change the hardness.

Figure 32A:
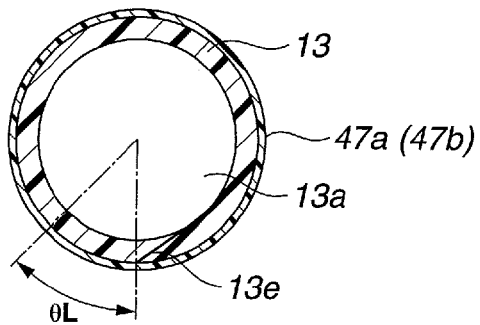
FIG. 32A is an A-A section of FIG. 28 and is a sectional view of the hardness changing portion before the deformation.
Figure 32B:
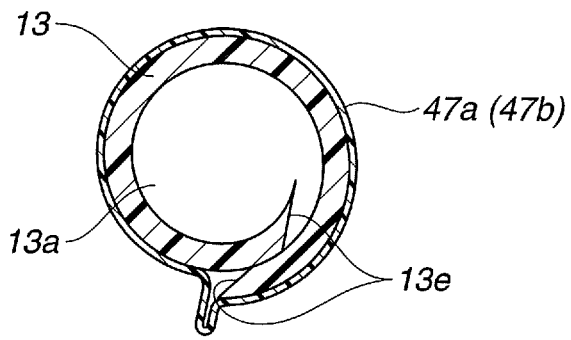
FIG. 32B is the A-A section of FIG. 28 and is a sectional view of the hardness changing portion after the deformation.
Figure 33A:
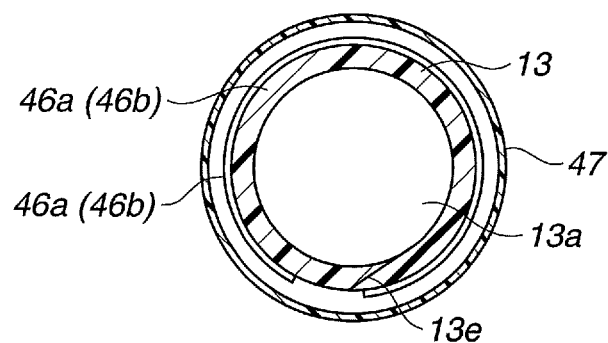
FIG. 33A is a B-B section of FIG. 28 and is a sectional view of the hardness changing portion before the deformation.

Specifically, as shown in FIGS. 27, 32A, 32B, 33A, and 33B, a slit portion 13e is formed along the major axis Lm from the distal end portion 13c of a surface opposed to the side hole 13b across the major axis Lm to a distal end region 13d including the rear portion of the side hole 13b. As shown in FIGS. 32A and 33A, this slit portion 13e is obliquely formed from the outer circumferential side surface to the inner circumferential surface of the tube main body 13.

Figure 30:
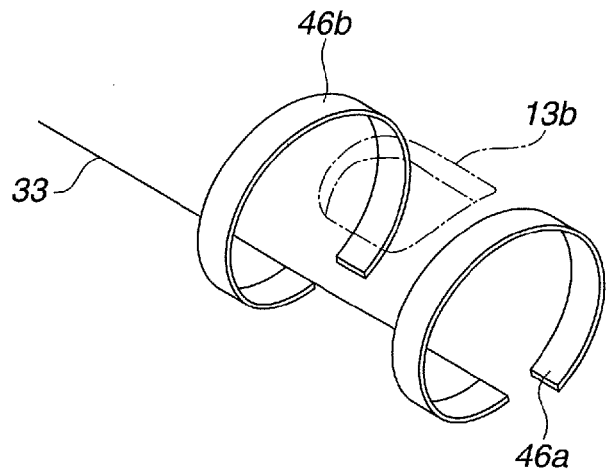
Figure 31:
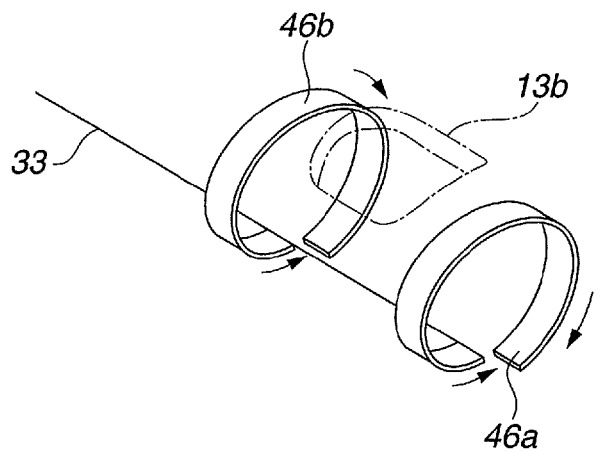
Figure 33B:
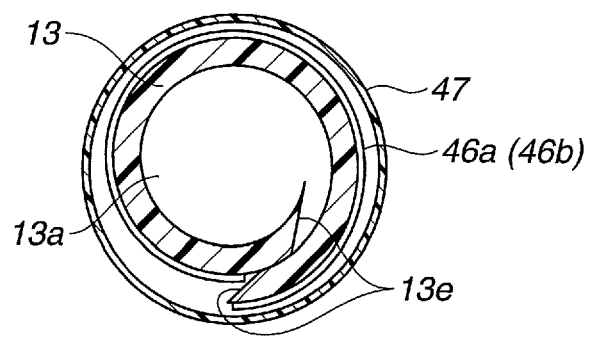

As shown in FIGS. 30 and 31, one ends of both the loop plates 46a and 46b are connected to the fixed contact point 34a (see FIG. 19) via the lead wire 33 and the other ends are grounded. As shown in FIGS. 30 and 33A, the loop plates 46a and 46b are, during non-energization, in a state in which both ends of the loop plates 46a and 46b are relatively separated from each other. As shown in FIGS. 31 and 33B, when energized, the loop plates 46a and 46b generate heat with internal resistance of the loop plates 46a and 46b and are displaced to the shape stored in advance, i.e., in a direction in which a space between both the ends of the loop plates 46a and 46b is narrowed.

Both the loop plates 46a and 46b are stuck to the outer circumferential side of the tube main body 13. As shown in FIG. 33B, when the loop plates 46a and 46b are displaced, the tube main body 13 is squeezed and both end faces forming the slit portion 13e of the tube main body 13 move in a direction in which both the end faces overlap.

Figure 29:
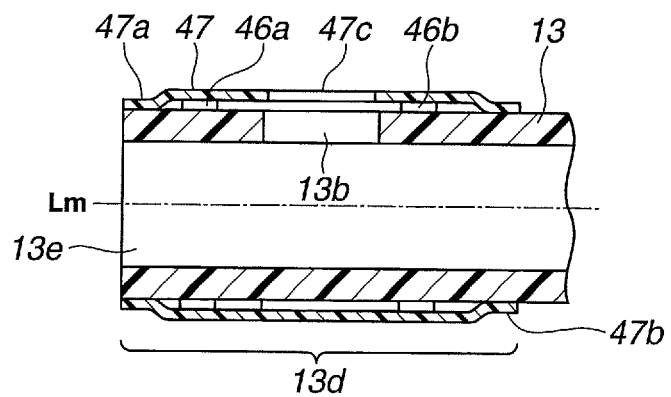

A distal end cover 47 is attached over an entire circumference of a region (the distal end region 13d) in which the slit portion 13e of the tube main body 13 is formed. As shown in FIGS. 29 and 30, both ends 47a and 47b of this cover 47 are bonded to the outer circumferential side of the tube main body 13. However, since the slit portion 13e overlaps when the loop plates 46a and 46b are displaced, as shown in FIG. 32A, the both the ends 47a and 47b are not bonded to a region θL slightly wider than a region of the overlap. Therefore, as shown in FIG. 32B, when the slit portion 13e overlaps, slack occurs in the region 8L not bonded. A relief hole 47c is formed in a region corresponding to the side hole 13b of the distal end cover 47.

In such a configuration, as shown in FIG. 19, in a state in which the rear end side inner surface of the stopper ring 26 is set in contact with the rear end of the pipe sleeve 25, a state of the movable contact point 34b and the fixed contact point 34a is an OFF state in which the movable contact point 34b is separated from the fixed contact point 34a. Therefore, as shown in FIG. 30, the pair of loop plates 46a and 46b provided on the distal end side of the tube main body 13 maintains an open state. Therefore, the distal end portion 13c side of the tube main body 13 is not squeezed and the flexibility is maintained.

On the other hand, as shown in FIG. 21, when the stopper ring 26 is pulled, the movable contact point 34b fixedly provided in the stopper ring 26 via the insulating collar 35 comes into contact with the fixed contact point 34a fixedly provided in the pipe sleeve 25. Electric power from the power supply 36 is supplied to both the loop plates 46a and 46b via the lead wire 33.

Then, both the loop plates 46a and 46b generate heat with internal resistance of the loop plates 46a and 46b. As shown in FIG. 31, the loop plates 46a and 46b are displaced to the shape stored in advance. Since the loop plates 46a and 46b are bonded to the outer circumferential side of the tube main body 13, the distal end region 13d of the tube main body 13 is rounded and squeezed by the displacement of the loop plates 46a and 46b. As a result, as shown in FIG. 33B, the thickness of the overlap region of the tube main body 13 increases. Therefore, the rigidity in the vertical axis Lv direction increases. When the distal end 3a of the insertion portion 3 provided in the cholangioscope 1 is projected from the side hole 13b formed on the surface substantially opposed to this overlap region, the tube main body 13 is less easily bent. The advancing direction of the insertion portion 3 can be accurately led in the choledoch B (see FIG. 8) direction.

When the distal end region 13d is rounded and squeezed by both the loop plates 46a and 46b, the distal end cover 47 attached on an outer circumference of this distal end region 13d changes to a slacked state as shown in FIG. 33B. Therefore, this distal end cover 47 is not bitten in the slit portion 13e.

Eighth Embodiment

An eighth embodiment of the present invention is shown in FIGS. 34A to 36B. In the present embodiment, the rigidity of the distal end portion 13c of the tube main body 13 is secured by a hardness changing portion 51 including plural dies 52.

Figure 35:
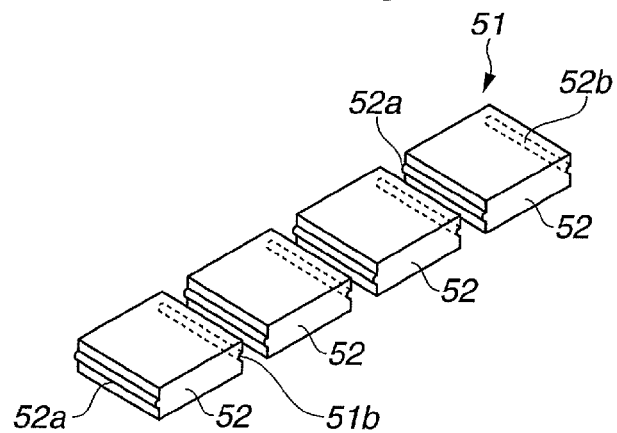

Specifically, the hardness changing portion 51 is disposed in the hardness changing chamber 31 formed on the surface opposed to the side hole 13b on the distal end side of the tube main body 13. This hardness changing portion 51 includes the plural dies 52. As shown in FIG. 35, in the dies 52, projections 52a of a semicircular shape in section extending in the width direction are formed in the front portions thereof and recesses 52b that engage with the projections 52a are formed in the rear portions thereof.

Figure 34A:
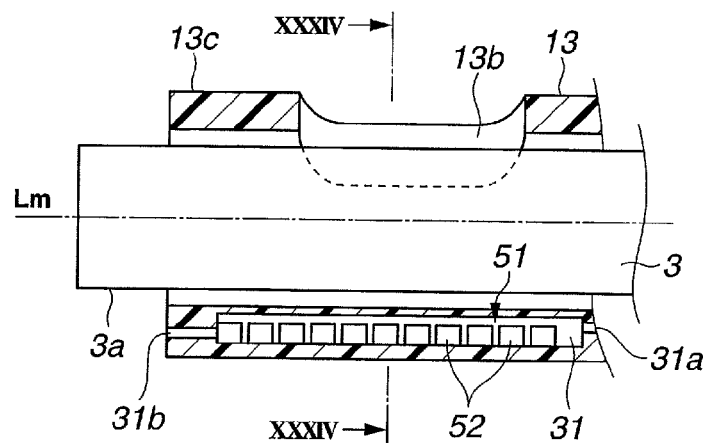
Figure 34B:
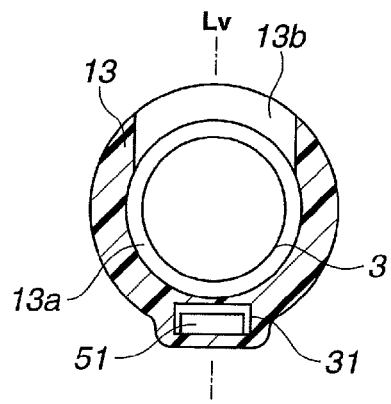
FIG. 34B is a XXXIV-XXXIV sectional view of FIG. 34A.

The dies 52 are allowed to move in the major axis Lm direction in the hardness changing chamber 31. As shown in FIGS. 34B and 36B, movement in the width direction (the left to right direction in the figure) is regulated by both wall surfaces of the hardness changing chamber 31.

An air lumen 31a is opened in the rear portion of this hardness changing chamber 31. A relief passage 31b that communicates with the outside is opened in the front portion thereof. This air lumen 31a is extended to the rear end of the tube main body 13 and caused to communicate with a not-shown air pump via a switching valve. This switching valve selectively causes the air from an air pump to communicate with the air lumen 31a and a passage that communicates with the atmosphere. In a switch OFF state in which the fixed contact point 34a provided in the fixing section 12 shown in FIG. 19 is in non-conductive to the movable contact point 34b, the switching valve causes the air pump to communicate with the atmosphere passage. On the other hand in a switch ON state in which the fixed contact point 34a is conductive to the movable contact point 34b, the switching valve causes the air pump and the air lumen 31a to communicate with each other. Therefore, in the switch ON state, compressed air from the air pump is sent into the hardness changing chamber 31 via the air lumen 31a. In FIG. 19, the lead wire 33 is connected to the fixed contact point 34a. However, in the present embodiment, it is assumed that this lead wire 33 is connected to an actuator that causes the switching valve to perform switching operation.

In such a configuration, as shown in FIG. 19, in a state in which the rear end side inner surface of the stopper ring 26 is set in contact with the rear end of the pipe sleeve 25, since the movable contact point 34b is separated from the fixed contact point 34a and the movable contact point 34b and the fixed contact point 34a are in the switch OFF state, the air pump is caused to communicate with the atmosphere passage. In a state in which the air pump is caused to communicate with the atmosphere passage, since the air is not sent into the hardness changing chamber 31, the dies 52 as the components of the hardness changing portion 51 are in a state in which the dies 52 are separated from one another as shown in FIGS. 34A and 34B. Therefore, the flexibility is maintained on the distal end portion 13c side of the tube main body 13.

On the other hand, as shown in FIG. 21, when the stopper ring 26 is pulled, the movable contact point 34b fixedly provided in this stopper ring 26 via the insulating collar 35 comes into contact with the fixed contact point 34a fixedly provided in the pipe sleeve 25 and electric power from the power supply 36 is supplied to the actuator via the lead wire 33. As a result, this actuator causes the switching valve to perform switching operation and causes the air pump to communicate with the air lumen 31a. The air from the air pump is blown out to the hardness changing chamber 31 via the air lumen 31a.

Figure 36A:
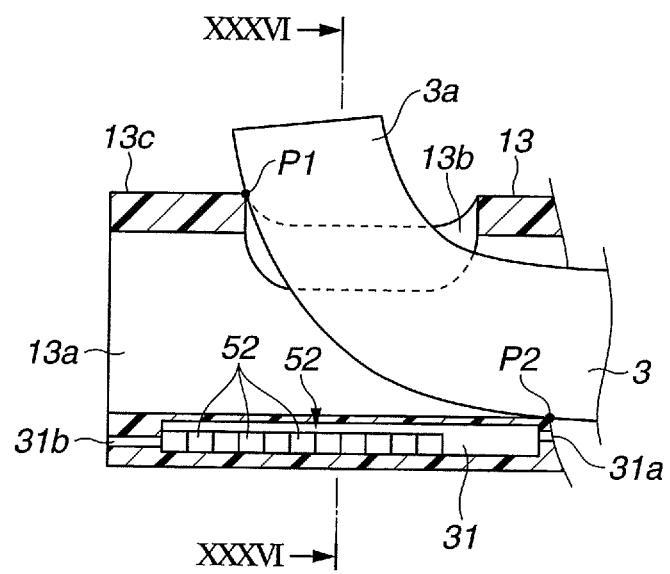
FIG. 36A is a sectional side view equivalent to FIG. 34A of a state in which the distal end portion of the medical tube is projected from a side hole of a tube main body.
Figure 36B:
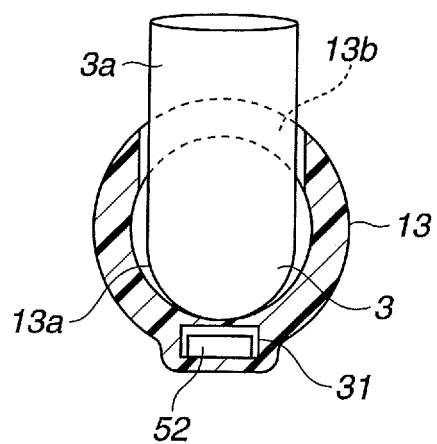

Then, as shown in FIGS. 36A and 36B, the backs of the dies 52 are pressed by the pressure of the air blown out from this air lumen 31a and pressed against the front wall of the hardness changing chamber 31. The projections 52a formed on the front surfaces of the dies 52 engage with the recesses 52b formed in the rear portions. The projections 52a and the recesses 52b are coupled to each other. The distal end portion 13c side is less easily bent in the vertical axis Lv direction. The rigidity on this distal end portion 13c side apparently increases.

As a result, when the distal end 3a of the insertion portion 3 provided in the cholangioscope 1 is projected from the side hole 13b of the tube main body 13, even if the distal end side edge portion P1 is pressed by this distal end 3a, the tube main body 13 is less easily bent. The advancing direction of the insertion portion 3 can be accurately led in the choledoch B (see FIG. 8) direction with the distal end side edge portion P1 of the side hole 13b as a fulcrum.

Ninth Embodiment

A ninth embodiment of the present invention is shown in FIGS. 37 to 40B. In the present embodiment, a reinforcing member 56 is disposed on the outer circumferential side of the tube main body 13. The strength on the distal end portion 13c side of the tube main body 13 is apparently changed by this reinforcing member 56.

Specifically, a ridge portion 13f is formed along the major axis Lm on the outer circumferential side on the opposite side opposed to the side hole 13b of the tube main body 13 across the major axis Lm. A support lumen 13g is formed in this ridge portion 13f. The reinforcing member 56 as a hardness changing portion is disposed in this support lumen 13g. This reinforcing member 56 has a reinforcing plate 57 inserted through the support lumen 13g to freely advance and retract and a leaf spring 58 that holds a distal end of this reinforcing plate 57. The distal end surface of the ridge portion 13f is located slightly further on the rear end side than the conduit supporting portion P2 (see FIG. 22).

Figure 40A:
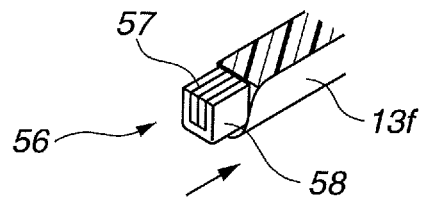
FIG. 40A is a perspective view showing a housed state of a support plate.
Figure 40B:
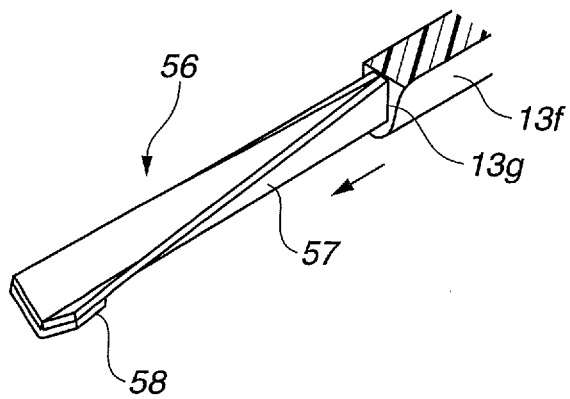
Figure 41:
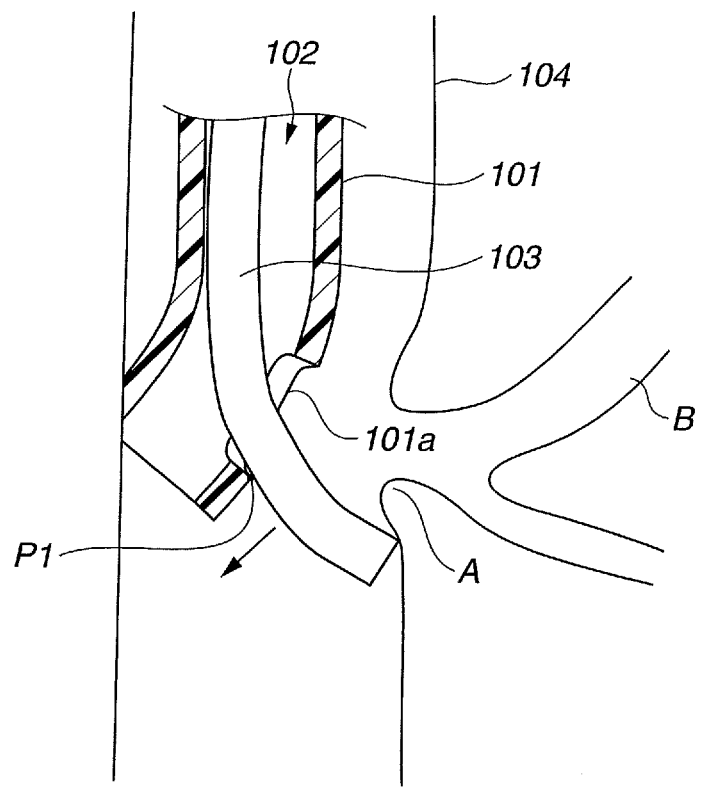
FIG. 41 is an explanatory diagram of a state in which an endoscope is led into a biliary tract in a transpapillary manner using a medical tube according to a conventional example.

The reinforcing plate 57 has a structure in which two flat plates made of metal having flexibility are joined. Rear ends of the flat plates are joined with each other in a joining portion 57a. Distal ends of the flat plates are jointed via the leaf spring 58. This reinforcing plate 57 is inserted through the support lumen 13g in a state in which the flat plates are joined with each other. As shown in FIG. 40A, the reinforcing plate 57 is housed in the support lumen 13g in a state in which the two flat plates included in the reinforcing plate 57 is joined with each other. Only the leaf spring 58 is projected on the distal end surface of the ridge portion 13f that forms this support lumen 13g. As shown in FIG. 40B, the leaf spring 58 has a shape opened in a V shape. As shown in FIG. 40A, in a state in which the reinforcing plate 57 is housed in the support lumen 13g, the leaf spring 58 is in a state in which the leaf spring 58 is closed in a C shape against the resilient force of the leaf spring 58.

A distal end of a push-out wire 59 is fixedly provided at a rear end of this reinforcing plate 57. A rear end of this push-out wire 59 is extended out to the fixing section 12 side shown in FIG. 1 through a wire lumen (not shown) formed in the tube main body 13 and is connected to a lever (not shown) provided in this fixing section 12. When the lever is pulled, the push-out wire 59 is pushed out. The reinforcing plate 57 housed in the support lumen 13g is pushed out and is projected in a state in which the reinforcing plate 57 is set in slide contact with the outer circumferential side of the tube main body 13.

In such a configuration, when the insertion portion 3 of the cholangioscope 1 is inserted per os in a state in which the insertion portion 3 is inserted in the conduit 13a of the tube main body 13, the reinforcing plate 57 is housed in the support lumen 13g formed in the ridge portion 13f. Moreover, the distal end surface of this ridge portion 13f is located slightly further on the rear end side than the conduit supporting portion P2 (see FIG. 22A). Therefore, the flexibility is maintained at the distal end portion 13c of the tube main body 13. Smooth insertability can be obtained.

When the side hole 13b opened in the tube main body 13 reaches near the duodenal papilla A (see FIG. 6), the insertion operation for the cholangioscope 1 is stopped. The lever (not shown) provided in the fixing section 12 is operated to push out the push-out wire 59. Then, the reinforcing plate 57 housed in the support lumen 13g is pushed out by this push-out wire 59.

The leaf spring 58 formed in a V shape is fixedly provided at the distal end of this reinforcing plate 57. Therefore, when the reinforcing plate 57 is projected from the support lumen 13g, the reinforcing plate 57 slides on the outer circumferential side of the tube main body 13 while the distal end side thereof is expanded in a V shape by the resilient force of the leaf spring 58.

Figure 37:
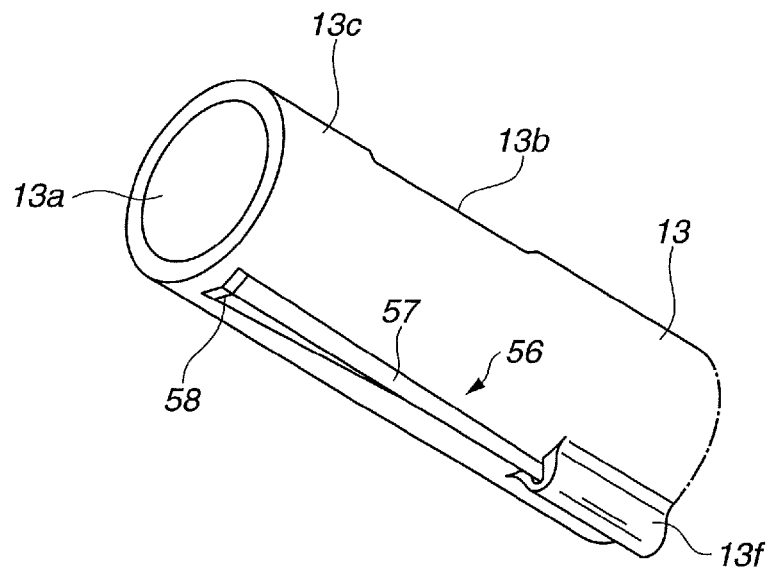
Figure 38A:
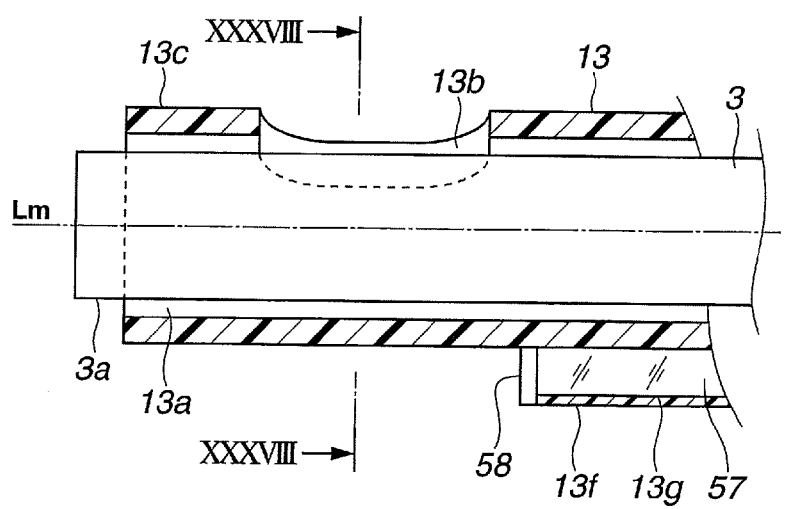
FIG. 38A is a sectional side view of the distal end portion of the medical tube.
Figure 38B:
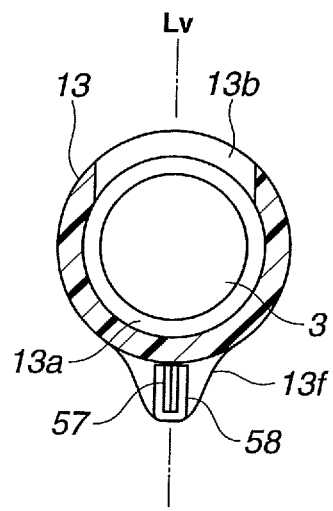
FIG. 38B is a XXXVIII-XXXVIII sectional view of FIG. 38A.
Figure 39A:
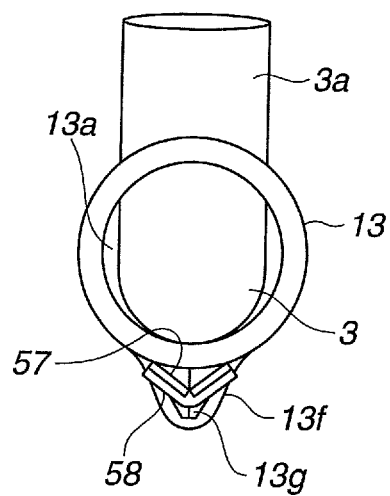
FIG. 39A is a front view of a state in which the distal end portion of the medical tube is projected from a side hole of a tube main body.
Figure 39B:
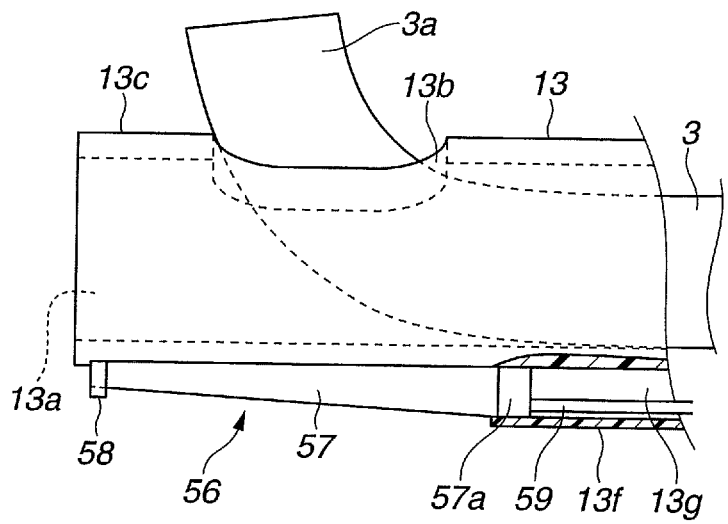
FIG. 39B is a main part right side view of FIG. 39A.

As shown in FIG. 37, the distal end of the reinforcing plate 57 is faced to the distal end portion 13c of the tube main body 13 and the joining portion 57a at the rear end is supported in the support lumen 13g. As a result, the outer circumferential side on the opposite side of the side hole 13b of the tube main body 13 is supported by this reinforcing plate 57 and bending in a direction opposite to the side hole 13b of this distal end portion 13c is regulated. As shown in FIGS. 39A and 39B, pressing force applied to the distal end side edge portion P1 at the time when the distal end 3a of the cholangioscope 1 projects from the side hole 13b can be supported.

In the present embodiment, the reinforcing plate 57 is housed in the support lumen 13g. When it is desired to reinforce the distal end portion 13c side of the tube main body 13, i.e., when apparent hardness is increased, the reinforcing plate 57 is projected. Therefore, a region to be bent of the distal end portion 13c can be freely set by adjusting an amount of this projection.

In the embodiments, the peroral endoscope is explained. However, it goes without saying that the present invention can also be applied to a percutaneous endoscope.

What is claimed is:

1. A medical tube comprising:
   a flexible and bendable tubular member through which a conduit, through which a medical instrument is insertable, is pierced from a distal end to a rear end; and
   a side hole that is formed between the distal end and the rear end of the tubular member and causes an outer circumferential side surface of the tubular member and the conduit to communicate with each other,
   wherein:
   the tubular member includes a hardness changing portion that deforms a sectional shape of the tubular member in a region distal to the side hole in a linear direction connecting an axial core of the tubular member and the side hole, thereby capable of increasing rigidity of the tubular member in the linear direction in a vicinity of the side hole, and the hardness changing portion includes a leaf spring, and changes rigidity of the tubular member with respect to bendability by expanding, with elasticity of the leaf spring, an outer diameter of the tubular member in a direction in which the side hole faces and reducing the outer diameter in a direction orthogonal to the side hole to deform the sectional shape of the tubular member, by nipping and integrating, with a resilient force of the leaf spring, a distal end portion of the medical instrument inserted through the hardness changing portion, and causing the distal end portion of the medical instrument to slip off from the hardness changing portion.

2. The medical tube according to claim 1, wherein the tubular member includes a portion on a distal end side, rigidity of which can be changed by the hardness changing portion, and a portion on a rear end side, rigidity of which is not changed by the hardness changing portion.

3. The medical tube according to claim 2, wherein a range in an axis direction of the tubular member, rigidity of which is changed by the hardness changing portion, is from an end on a distal end side of the side hole to a portion that comes into contact with an inner surface of the conduit when the medical instrument bends toward the side hole in a state in which the medical instrument is projected from the side hole.

4. The medical tube according to claim 1, wherein the hardness changing portion has a core member disposed along a major axis of the tubular member and changes a sectional shape in a direction crossing a major axis of the core member to change rigidity of the tubular member with respect to bendability.

5. The medical tube according to any one of claim 1, further comprising a fixing mechanism for fixing the medical instrument inserted through the conduit, wherein the hardness changing portion changes the rigidity of the tubular member according to release of the fixing by the fixing mechanism.

6. The medical tube according to claim 1, wherein the hardness changing portion includes a pair of leaf springs provided in a diametrical direction connecting the side hole and the axial core of the tubular member.

7. A medical tube comprising:
a flexible and bendable tubular member;
a conduit through which a medical instrument is insertable, the conduit being formed inside the tubular member;
a distal end opening portion through which the medical instrument is projectable, the distal end opening portion being provided at a distal end of the tubular member to communicate with the conduit and capable of opening/closing;
a side hole through which the medical instrument is projectable, the side hole being formed on an outer circumferential side surface of the tubular member to communicate with the conduit; and
a hardness changing portion including a pair of leaf springs provided at the distal end opening portion and in a diametrical direction connecting the side hole and an axial core of the tubular member, wherein the hardness changing portion changes rigidity of the tubular member with respect to bendability by expanding an outer diameter of the tubular member in a direction in which the side hole face and reducing the outer diameter in a direction orthogonal to the side hole to deform the sectional shape of the tubular member, by nipping and integrating, with a resilient force of the pair of leaf springs, a distal end portion of the medical instrument inserted through the hardness changing portion, and causing the distal end portion of the medical instrument to slip off from the hardness changing portion.

8. A medical tube comprising:
a flexible and bendable tubular member through which a conduit, through which a medical instrument is insertable, is pierced from a distal end to a rear end; and
a side hole that is formed between the distal end and the rear end of the tubular member and causes an outer circumferential side surface of the tubular member and the conduit to communicate with each other,
wherein:
the tubular member includes a hardness changing portion that deforms a sectional shape of the tubular member in only a region distal to the side hole in a linear direction connecting an axial core of the tubular member and the side hole, thereby capable of increasing rigidity of the tubular member in the linear direction in a region distal to the side hole, and
the hardness changing portion includes a leaf spring, and changes rigidity of the tubular member with respect to bendability by expanding an outer diameter of the tubular member in a direction in which the side hole face and reducing the outer diameter in a direction orthogonal to the side hole to deform the sectional shape of the tubular member, by nipping and integrating, with a resilient force of the leaf spring, a distal end portion of the medical instrument inserted through the hardness changing portion, and causing the distal end portion of the medical instrument to slip off from the hardness changing portion.

* * * * *